United States Patent
Van Den Berghe et al.

(10) Patent No.: US 7,491,187 B2
(45) Date of Patent: Feb. 17, 2009

(54) AUTOMATIC INFUSION SYSTEM BASED ON AN ADAPTIVE PATIENT MODEL

(75) Inventors: Greta Van Den Berghe, Grez-Doiceau (BE); Daniel Berckmans, Kessel-Lo (BE); Jean-Marie Aerts, Haasrode (BE); Bart De Moor, Bierbeek (BE); Bert Pluymers, Westerlo (BE); Frank De Smet, Mechelen (BE)

(73) Assignee: K.U. Leuven Research & Development, Leuven (BE)

( * ) Notice: Subject to any disclaimer, the term of this patent is extended or adjusted under 35 U.S.C. 154(b) by 283 days.

(21) Appl. No.: 10/508,572

(22) PCT Filed: Mar. 24, 2003

(86) PCT No.: PCT/BE03/00050

§ 371 (c)(1), (2), (4) Date: Feb. 22, 2005

(87) PCT Pub. No.: WO03/080157

PCT Pub. Date: Oct. 2, 2003

(65) Prior Publication Data

US 2005/0171503 A1     Aug. 4, 2005

(30) Foreign Application Priority Data

Mar. 22, 2002  (GB) ................................ 0206792.4

(51) Int. Cl.
    A61M 5/30    (2006.01)
(52) U.S. Cl. .............................. 604/66; 604/504; 700/28
(58) Field of Classification Search ............. 604/65–67, 604/504; 700/28–31, 44–45; 702/22–23, 702/85–86, 104

See application file for complete search history.

(56) References Cited

U.S. PATENT DOCUMENTS

| | | | | |
|---|---|---|---|---|
| 4,055,175 A | * | 10/1977 | Clemens et al. | 604/66 |
| 4,280,494 A | * | 7/1981 | Cosgrove et al. | 604/503 |
| 5,971,922 A | * | 10/1999 | Arita et al. | 600/365 |

(Continued)

FOREIGN PATENT DOCUMENTS

EP        0 806 738        *  5/1997

(Continued)

OTHER PUBLICATIONS

Bellazi et al., "The Subcutaneous Route to Insulin-Dependent Diabetes Therapy: Closed-Loop and Partially Closed-Loop Control Strategies for Insulin Delivery and Measuring Glucose Concentration," IEEE Engineering in Medicine and Biology, 54-64 (Jan./Feb. 2001).*

(Continued)

*Primary Examiner*—Nicholas D. Lucchesi
*Assistant Examiner*—Theodore J Stigell
(74) *Attorney, Agent, or Firm*—Clark & Elbing LLP

(57) ABSTRACT

Present invention is a system of blood glucose monitoring and intensive insulin therapy in a ICU for strict maintenance of normoglycemia which reduces intensive care and hospital mortality and morbidity of critically ill adult patients. The findings of present study also reveal factors determining insulin doses needed to maintain normoglycemia as well as the impact of insulin dose versus blood glucose level on the observed outcome benefits have been established. The invention provides a control system that adapts the flow of the insulin infusion based on insulin requirement calculated by blood glucose levels and clinical parameters such as history of diabetes, Body Mass Index, blood glucose level on admission, reason of ICU admission, time in the ICU, type and severity of illness, caloric intake, obesity, drugs affecting insulin sensitivity). This automated insulin monitoring systems significantly reduces the workload and human resource management problems for intensive insulin therapy in patients in the ICU.

17 Claims, 8 Drawing Sheets

U.S. PATENT DOCUMENTS

| | | | |
|---|---|---|---|
| 6,017,318 A | | 1/2000 | Gauthier et al. |
| 6,544,212 B2 * | | 4/2003 | Galley et al. .................. 604/31 |
| 6,558,351 B1 * | | 5/2003 | Steil et al. .................... 604/131 |
| 6,572,542 B1 * | | 6/2003 | Houben et al. .............. 600/300 |
| 6,656,114 B1 * | | 12/2003 | Poulsen et al. .............. 600/300 |

FOREIGN PATENT DOCUMENTS

| | | | |
|---|---|---|---|
| EP | 0806738 A1 | | 11/1997 |
| WO | WO 00/74753 | | 12/2000 |
| WO | WO 01/83007 | * | 11/2001 |

OTHER PUBLICATIONS

Parker et al., The Intravenous Route to Blood Glucose Control: A Review of Control Algorithms for Noninvasive Monitoring and Regulation in Type I Diabetic Patients, IEEE Engineering in Medicine and Biology, 65-73 (Jan./Feb. 2001 ).*

Parker et al., "The Intravenous Route to Blood Glucose Control: A Review of Control Algorithms for Noninvasive Monitoring and Regulation in Type I Diabetic Patients," *IEEE Engineering in Medicine and Biology*, 65-73 (Jan./Feb. 2001).

Van den Berghe et al., "Intensive Insulin Therapy in Critically Ill Patients," The New England Journal of Medicine, 345(19): 1359-1367 (2001).

Communication from European Patent Office for European Patent Application No. EP 03 711 717.3 dated Sep. 18, 2008.

* cited by examiner

Principle of an automated model-based insulin controller.
* disturbances: BMI, history of diabetes, reason for ICU admission, severity of illness, on-admission hyperglycemia, caloric intake, time in ICU and concomitant medication (glucocorticoids)

AUTOMATIC INFUSION SYSTEM BASED ON AN ADAPTIVE PATIENT MODEL

CROSS REFERENCE TO RELATED APPLICATIONS

This application is the U.S. National Stage of International Application No. PCT/BE03/00050, filed Mar. 24, 2003, which, in turn, claims the benefit of GB 0206792.4, filed Mar. 22, 2002.

FIELD OF THE INVENTION

This invention relates to algorithmic control of insulin titration and blood glucose monitoring for reducing intensive care and hospital mortality and morbidity (such as critical illness polyneuropathy, bacteremia, inflammation and anemia) of critically ill patients in an ICU, preferably a surgical ICU. More specifically present invention involves an algorithm and a system to reduce mortality and morbidity in critically ill patients (who require intensive care) through a software-assisted control of glycemia (concentration of glucose in the blood).

TECHNICAL BACKGROUND

Hyperglycemia and insulin resistance are common in critically ill patients, even when glucose homeostasis has previously been normal. Increased gluconeogenesis, despite abundantly released insulin, is probably central to this disruption of glucoregulation (Wolfe R R, et al Metabolism 1979; 28: 210-220 Wolfe R R, et al. N Engl J Med. 1987; 317; 403-408).

Hence, the liver appears a major site of insulin resistance. Reduced insulin-stimulated glucose uptake also exists in skeletal muscle and heart (Wolfe R R, et al Metabolism 1979; 28: 210-220, Shangraw R E, et al. Metabolism 1989; 38: 983-9893). Overall glucose uptake, however, is increased but takes place mainly in insulin-independent tissues such as the brain, the red blood cells and in wounds. The increased glucose turnover and insulin-resistance of hyperglycemia were previously interpreted as a plea for tolerating moderately elevated ($\leqq$215 mg/dl) blood glucose levels during critical illness (Mizock B A. et al. Am J Med. 1995; 98:75-84; McCowen K C, et al. Crit Care Clin. 2001; 17: 107-124). More pronounced hyperglycemia in diabetic surgical patients has been associated with high incidence of postoperative infections (Fietsam R jr, et al. Am Surg. 1991; 57: 551-557) and after stroke and head injury with poor prognosis (O'Neill P A, Davies I, Scott J F, et al. Stroke 1999). In diabetic patients suffering from acute myocardial infarction, blood glucose control below 215 mg/dl has been shown to improve long-term outcome (Malmberg K, et al. Circulation. 1999; 99: 2626-2632; Malmberg K BMJ 1997; 314: 1512-1515; Malmberg K, et al. J Am Coll Cardiol. 1995; 26: 57-65). We recently hypothesized that even moderate hyperglycemia, between 110 mg/dl and 200 mg/dl, in diabetic as well as in non-diabetic critically ill patients is directly or indirectly harmful to vital organs and systems (Van den Berghe G, et al. N Engl J Med. 2001; 345: 1359-1367) hence contributing to adverse outcome. A prospective, randomized, controlled study performed in 1548 ICU patients confirmed this hypothesis by showing that strict glycemic control below 110 mg/dl with insulin infusion substantially reduces morbidity and mortality (Van den Berghe G, et al. N Engl J Med. 2001; 345: 1359-1367). Indeed, intensive insulin therapy reduced overall ICU mortality from 8% to 4.6%, and from 20.2% to 10.6% among patients requiring more than 5 days intensive care. Intensive insulin therapy also halved the incidence of blood stream infections, prolonged inflammation, acute renal failure requiring dialysis or hemofiltration, critical illness polyneuropathy and transfusion requirements. Patients receiving intensive insulin therapy were also less likely to require prolonged mechanical ventilation and intensive care. It remained an open question, however, whether the benefits are brought about directly by the infused insulin per se or by the prevention of hyperglycemia, as both occurred concomitantly.

Present findings clearly demonstrate that strict maintenance of normoglycemia with intensive insulin therapy reduces intensive care and hospital mortality and morbidity of critically ill adult patients in a surgical ICU. The findings of present study also reveal factors determining insulin doses needed to maintain normoglycemia as well as the impact of insulin dose versus blood glucose level on the observed outcome benefits have been established.

By a prospective, randomized, controlled trial in a single center in a 56-bed predominantly surgical ICU in a tertiary teaching hospital 1548 patients were randomly assigned to either strict normalization of blood glucose (80-110 mg/dl) with intensive insulin therapy from ICU admission onward or the conventional approach, in which insulin infusion is only initiated when blood glucose exceeds 215 mg/dL, to maintain blood glucose levels between 180 and 200 mg/dl. It was feasible and safe to achieve and maintain blood glucose levels below 110 mg/dL by using a simple insulin titration algorithm which takes on-admission patient- and disease-related factors such as BMI, history of diabetes, reason for ICU admission, severity of illness, on-admission hyperglycemia, as well as the caloric intake, time in ICU and concomitant medication (glucocorticoids) into account. Stepwise regression analysis indicated that, except for severity of illness and use of glucocorticoids, all these factors were independent determinants of mean insulin requirements, together explaining 36% of its variation. Nutritional intake was progressively increased from a mean 550 Cal on day 1 to a mean 1600 Cal from day 7 onward. The dose of insulin required to reach normoglycemia was highest and most variable during the first 6 hours after admission (a mean of 7 units per hour; 10% of the patients required more than 20 units per hour). Normoglycemia was reached within 24 h with, for a 70 kg patient, a mean 77 units per day on the first day and 94 units per day on day 7. Between day 7 and 12, caloric intake remained stable but insulin requirements decreased by 40%. Brief and clinically harmless hypoglycemia occurred in 5.2% of intensive insulin treated patients on the median $6^{th}$ (IQR $2^{nd}$-$14^{th}$) day versus in 0.8% of the conventionally treated patients on the $11^{th}$ ($2^{nd}$-$10^{th}$) day.

The observed benefits of intensive insulin therapy on morbidity and mortality were equally present whether or not patients received enteral feeding. The lowered blood glucose level rather than the insulin dose was related to the observed reduction in mortality (P<0.0001), critical illness polyneuropathy (P<0.0001), bacteremia (P=0.02) and inflammation (P=0.0006) but not to the prevention of acute renal failure, for which the insulin dose was an independent determinant (P=0.03). Among long-stay patients, maintaining strict normoglycemia appeared important for optimal risk reduction as intermediate (110-150 mg/dl) blood glucose levels were associated with a significantly higher incidence of most intensive care complications and death.

It has now demonstrated by that glycemia between 80 and 110 mg/dl (4.4 and 6.1 mmol/l), through a rigorous administration of insulin (intensive insulin therapy) can result in a spectacular reduction in mortality and morbidity. This major step forward in the treatment of critically ill patients, particularly since most large clinical trials on immunomodulatory treatment of sepsis and shock failed to demonstrate benefit.

However, intensive monitoring with fast and easy access of blood glucose may be a useful in order to accurately steer the delivery of insulin or insulin releasing factors. Malberg K. A., et al. 1994 (Diabetes Care 17: 1007-1014 (1994)), for instance, demonstrated that in a study of glucose control following myocardial infarction that infusion with insulin and glucose resulted in 18% of the patients developing hypoglycemia. A hypoglycemia defined as blood glucose below 0.3 mM/litre, is for instance known to increases risk of myocardial infarction and ventricular arrhythmia.

Moreover, Sakuri Y. et al. (Annals of surgery Vol. 222 No. 3 283-297 (1995)) demonstrated that burned patients have a negative balance between protein synthesis and breakdown, despite a nutritional intake and concluded that mechanism responsible for this imbalance was principally a high rate of protein breakdown. Sakuri Y. et al. Found that chronic insulin delivery 28 units/hour, could increase the protein breakdown. Although this striking finding that insulin infusion increases protein breakdown, in healthy volunteers as well in burned patients insulin delivery ameliorated the net catabolism of muscle protein. Sakuri K. A. et al concluded that for treatment of burned patient by insulin a lower dose would be preferable because of the potential problems of giving a caloric overload with high glucose dose insulin and because avoiding hypoglycemia such high dose treatment would be too clinical demanding. Moreover, Ferrando, -A-A; et al. (Ann-Surg. 1999 January; 229(1): 11-8) in an attempt to reverse the net muscle catabolism associated with severe burns, demonstrated that if large quantities of exogenous glucose required to maintain euglycemia, and hypoglycemia in patients with severe burns promoted skeletal muscle glucose uptake and net protein synthesis but was associated with caloric overload, suggesting an hidden hypoglycemia.

This demonstrates that intensive insulin treatment of critical ill patients for safety and efficacy of insulin and nutrient infusion therapy not only requires an intensive monitoring of blood glucose concentrations with easy and rapid access to blood glucose data and that a clear prediction per patient of the biological response to a given concentration of insulin van optimize the intensive insulin therapy of critical ill patients or subjects with insulin resistance or increased glucose uptake.

Present invention allows now to predict insulin requirement to maintain normoglycemia in an intensive care patient and to predict the impact of insulin dose versus blood glucose level on the observed outcome benefits.

Present inventions now reveals predictive factors that determine insulin doses needed to maintain normoglycemia as well as the impact of insulin dose versus glucose level on the observed outcome of benefit. Date of this invention the administration of insulin in intensive care patients can now be controlled by a titration protocol, the general guidelines for this protocol are given in the titration algorithm of this application. However, this protocol is still labor intensive.

However a second embodiment of present invention provides a control system that adapts the flow of the insulin infusion based on insulin requirement calculated by blood glucose levels and clinical parameters such as history of diabetes, Body Mass Index, blood glucose level on admission, reason of ICU admission, time in the ICU, type and severity of illness, caloric intake, obesity, drugs affecting insulin sensitivity. This automated insulin monitoring systems for intensive insulin therapy in patients in the ICU significantly reduces the workload and human resourse management problems and improves patient survivability.

This system can advise the medical team about the desired insulin administration rate or can apply a more automatic control. It has the following properties:

1. In the initial phase (first 24 h) the hyperglycemia is reduced, as quickly as possible, to stable normoglycemia without causing hypoglycemia.
2. The control system is robust (i.e., the blood glucose level is as stable as possible) against complicating factors (e.g., concomitant infection) and changing circumstances (e.g., decreasing insulin resistance, other route of feeding, change in medication, . . . ).

SUMMARY OF THE PRESENT INVENTION

Present findings clearly demonstrate that strict maintenance of normoglycemia with intensive insulin therapy reduces intensive care and hospital mortality and morbidity of critically ill adult patients in a surgical ICU. The findings of present invention reveal factors determining insulin doses needed to maintain normoglycemia as well as the impact of insulin dose versus blood glucose level on the observed outcome benefits have been established.

By a prospective, randomized, controlled trial in a single center in a 56-bed predominantly surgical ICU in a tertiary teaching hospital 1548 patients were randomly assigned to either strict normalization of blood glucose (80-110 mg/dl) with intensive insulin therapy from ICU admission onward or the conventional approach, in which insulin infusion is only initiated when blood glucose exceeds 215 mg/dL, to maintain blood glucose levels between 180 and 200 mg/dl. It was feasible and safe to achieve and maintain blood glucose levels below 110 mg/dL by using an insulin titration algorithm which takes on-admission patient- and disease-related factors such as Body Mass Index (BMI), history of diabetes, reason for ICU admission, severity of illness, on-admission hyperglycemia, as well as the caloric intake, time in ICU and concomitant medication (glucocorticoids) into account.

Stepwise regression analysis indicated that, except for severity of illness and use of glucocorticoids, all these factors were independent determinants of mean insulin requirements, together explaining 36% of its variation.

Nutritional intake was progressively increased from a mean 550 Cal on day 1 to a mean 1600 Cal from day 7 onward. The dose of insulin required to reach normoglycemia was highest and most variable during the first 6 hours after admission (a mean of 7 units per hour; 10% of the patients required more than 20 units per hour). Normoglycemia was reached within 24 h with, for a 70 kg patient, a mean 77 units per day on the first day and 94 units per day on day 7. Between day 7 and 12, caloric intake remained stable but insulin requirements decreased by 40%. Brief and clinically harmless hypoglycemia occurred in 5.2% of intensive insulin treated patients on the median 6th (IQR 2nd-14th) day versus in 0.8% of the conventionally treated patients on the 11th (2nd-10th) day.

The observed benefits of intensive insulin therapy on morbidity and mortality were equally present whether or not patients received enteral feeding. The lowered blood glucose level rather than the insulin dose was related to the observed reduction in mortality (P<0.0001), critical illness polyneuropathy (P<0.0001), bacteremia (P=0.02) and inflammation (P=0.0006) but not to the prevention of acute renal failure, for which the insulin dose was an independent determinant (P=0.03). Among long-stay patients, maintaining strict normoglycemia appeared important for optimal risk reduction as intermediate (110-150 mg/dl) blood glucose levels were associated with a significantly higher incidence of most intensive care complications and death.

This study clearly demonstrates that normoglycemia can safely reached within 24 h and maintained during intensive care by using simple insulin titration guidelines.

Metabolic control, as reflected by glycemia below 110 mg/dl, rather than the infused insulin dose was related to the observed protective effects of intensive insulin therapy on morbidity and mortality.

A second embodiment of present invention involves a control system that adapts the flow of the insulin infusion based on insulin requirement calculated by blood glucose levels and clinical parameters such as history of diabetes, Body Mass Index, blood glucose level on admission, reason of ICU admission, time in the ICU, type and severity of illness, caloric intake, obesity, drugs affecting insulin sensitivity.

This automated insulin monitoring systems for intensive insulin therapy in patients in the ICU significantly reduces the workload and human resourse management problems and improves patient survivability.

This system can advise the medical team about the desired insulin administration rate or can apply a more automatic control. It has the following properties:
1. In the initial phase (first 24 h) the hyperglycemia is reduced, as quickly as possible, to stable normoglycemia without causing hypoglycemia.
2. The control system is robust (i.e., the blood glucose level is as stable as possible) against complicating factors (e.g., concomitant infection) and changing circumstances (e.g., decreasing insulin resistance, other route of feeding, change in medication, . . . ).

Definitions

The term "systemic inflammatory response syndrome (SIRS)", as used herein refers to the uncontrolled disease process which ensues an initial insult and which gives rise to a multi system disturbance secondary to inflammatory mediators released during shock.

The term "sepsis", as used herein refers to "SIRS", as described above, which is particularly caused by an infectious insult leading to the initial shock phase.

The term "mediators of sepsis", as used herein refers to factors released by inflammatory cells, such as TNFs, intedeukins, bradykinins etc.

The term "insulin receptor type tyrosine kinase", as used herein refers to a post-receptor signal transduction pathway involved in the insulin signaling.

The term "endoneural edema", as used herein refers to swelling of the neuronal cells.

The term "phrenic nerves", as used herein refers to the left and right nervus phrenicus, innervating the diaphragm.

The term "blood glucose regulator", as used herein refers to any compound which is able to regulate the blood glucose level. Examples of blood glucose regulators are insulin, active insulin derivatives, insulin analogues, glucagon like peptide 1 or its functional derivatives, compounds that stimulate signal transduction mediated by an insulin receptor type tyrosine kinase in a cell, certain protein-tyrosine phosphatases (PTP's), other type II antidiabetica, and other biologically active substances having insulin releasing action.

The term "Glucagon like peptide 1 (GLP-1)" as used herein is a incretin hormone.

This is processed from proglucagon in the gut and enhances nutrient-induced insuline release (Krcymann B., et al., Lancet 2: 1300-1303 (1987)). Various truncated forms of GLP-1, particularly GLP-1 (7-36) amide and GLP-1 (7-37) acid, are known to stimulate insuline secretion (Mojsov S. Int. J. Peptide Protein Research 40: 333-343 (1992)); Nauck M. A., et al. Diabetologia 36: 741-744 (1993); Nauck M. A., et al. J. Clin. Invest. 91: 301-307 (1993); Gutniak, M. et al., New England J. of Medicine 326 (20): 1316-1322 (1992) and Thorens B., et al. Diabetes 42: 1219-1225 (1993)). Various compounds are known to stimulate secretion of endogenous GLP-I. For example, exposure of STC-I cells to certain secretagogues, such as, the adenylate cyclase activator, forskolin, or the protein kinase-C-stimulating agent, 12-O-tetradecanoylphobol-13-acetate (TPA), caused significant increases in release of GLP-1 (Abello Jr. et al., Endocrinol. 134: 2011-2017a (1994)). The STC-1 cell line originated from an intestinal tumor in transgenic mice carrying insulin-promoting oncogenes, and STC-1 cells are known to contain mRNA transcripts of pro-glucagon, from which GLP-1 is generated. Other compounds, such as, somatostatin, gastric inhibitor polypeptide, glucose-dependent insulinotropic peptide, bombesin, calcitonin gene-related peptide, gastrin-releasing peptide, cholinergic agonists, the P-adrenergic agonist, isoproterenol, and the muscarinic cholinergic agonist, bethanechol, are similarly known to cause release of endogenous GLP-1 (Plaisancie et al., Endocrinol. 135: 2348-2403 (1994)), Orskov et al., Endocrinol. 119: 1467-1475 (1986), Brubaker, P. L. Endocrinol. 128: 3175-03182 (1991), Buchan A. M. J. et al., Gastroenterol. 93: 971-800 (1987).

The term "insulin", as used herein refers to insulin from any species such as porcine insulin, bovine insulin, and human insulin and salts thereof such as zinc salts, and protamin salts.

The term "active derivatives of insulin", as used herein are what a skilled art worker generally considers derivatives, vide general textbooks, for example, insulin having a substituent not present in the parent insulin molecule.

The term "insulin analogues", as used herein refers to insulin wherein one or more of the amino acid residues have been exchanged with another amino acid residue and/or from which one or more amino acid residue has been deleted and/or from which one or more amino acid residue has been added with the proviso that said insulin analogue has a sufficient insulin activity. Using results from the so-called free fat cell assay, any skilled art worker, for example, a physician, knows when and which dosages to administer of the insulin analogue. Examples of insulin analogues are described in the following patents and equivalents thereto: U.S. Pat. No. 5,618,913, EP 254,516, EP 280,534, U.S. Pat. Nos. 1 5 5,750, 497, and 6,011,007. Examples of specific insulin analogues are insulin aspart (i.e., AspB$^{128}$ human insulin), insulin lispro (i.e., LyS$^{B28}$, Pro$^{B29}$ human insulin), and insulin glagin (i.e., Gly$^{A21}$ Arg$^{B31}$,Arg$^{B32}$ human insulin). Also compounds which can be considered being both an insulin derivative and an insulin analogue can be used to practice the present invention. Examples of such compounds are described in the following patents and equivalents thereto: U.S. Pat. Nos. 51,750, 497 and 6,011,007. An example of a specific insulin analogues and derivatives is insulin detenir (i.e., des-Thr$^{B30}$ human insulin y LyS$^{B29}$ tetradecanoyl).

The term "non-diabetic patient", as used herein refers to a patient who has not been diagnosed as having diabetes.

In its broadest sense, the term a "critically ill patient" (herein designated CIP), As used herein refers to a patient who has sustained or are at risk of sustaining acutely life-threatening single or multiple organ system failure due to disease or injury, a patient who is being operated and where complications supervene, and a patient who has been operated in a vital organ within the last week or has been subject to major surgery within the last week. In a more restricted sense, the term a "critically ill patient", as used herein refers to a patient who has sustained or are at risk of sustaining acutely life-threatening single or multiple organ system failure due to disease or injury, or a patient who is being operated and where complications supervene. In an even more restricted sense, the term a "critically ill patient", as used herein refers to a patient who has sustained or are at risk of sustaining acutely life-threatening single or multiple organ system failure due to disease or injury. A critically ill patient can be a patient who needs vital organ support (either mechanically such as with mechanical ventilation or dialysis etc. or pharmacologically such as with inotropes or vasopressors) without which they would not survive.

Similarly, these definitions apply to similar expressions such as "critical illness in a Patient" and a "patient is critically ill".

The term "Hyperglycaemia" means a greater than normal concentration of glucose in the blood.

The term normolglycemia" as used herein means a blood glucose between 60 and 130 mg/dl, more preferably between 70 and 120 mg/dl and most preferably between 80 and 110 mg/dl.

The term "insulin resistance" as used herein, refers to a subnormal biological response to a given concentration of insulin. Insulin resistance is generally characterised by the requirement of inappropriately high levels of insulin for maintaining glucose homeostasis.

"Increased glucose turnover" is an disproportionate increase in glucose turnover Injury increases whole-body glucose turnover and whole-body glucose recycling (%). The increased glucose turnover may be seen as a way of optimising host defenses and ensuring wound repair by providing essential fuel for inflammatory and reparative tissue.

The terms "monomeric human insulin analog" "monomeric insulin analog" and "human insulin analog" are well-known in the art, and refer generally to fast-acting analogs of human insulin, which include human insulin, wherein Pro at position B28 is substituted with Asp, Lys, Leu, Val, or Ala, and wherein position B29 is Lys or is substituted with Pro; AlaB26-human insulin des(B28-B30) human insulin; and des (B27) human insulin. Such monomeric insulin analogs are disclosed in Chance, et al., U.S. Pat. No. 5,514,646, issued May 7, 1996; Chance, et al., U.S. patent application Ser. No. 08/255,297; Brems, et al., Protein Engineering, 6:527-533 (1992); Brange, et al., EPO publication No. 214,826 (published Mar. 18, 1987); and Brange, et al., Current Opinion in Structural Biology 1:934-940 (1991). The monomeric insulin analogs employed in the present formulations are properly crosslinked. A properly cross-linked insulin analog contains three disulfide bridges: one between position 7 of the A chain and position 7 of the B-chain, a second between position 20 of the A-chain and position 19 of the B-chain, and a third between positions 6 and 11 of the A-chain.

The term "insulin regulating" as used herein, refers to an ability to control the release of insulin into the circulation, in relation to blood glucose and fatty acid levels.

The term "pharmaceutically acceptable carrier or adjuvant" as used herein, refers to a non-toxic carrier or adjuvant that may be administered to a patient together with a compound of the invention, and which does not destroy the pharmacological activity thereof.

The terms "therapeutically or pharmaceutically effective" or "therapeutically or pharmaceutically effective amount" refers to an amount of the compound of this invention required to improve the clinical symptoms.

The term "Intensive Care Unit" (herein designated ICU), as used herein refers to the part of a hospital where critically ill patients are treated. Of course, this might vary from country to country and even from hospital to hospital and said part of the hospital may not necessary, officially, bear the name "Intensive Care Unit" or a translation or derivation thereof. Of course, the term "Intensive Care Unit" also covers a nursing home a clinic, for example, a private clinic, or the like if the same or similar activities are performed there.

Figure 1:
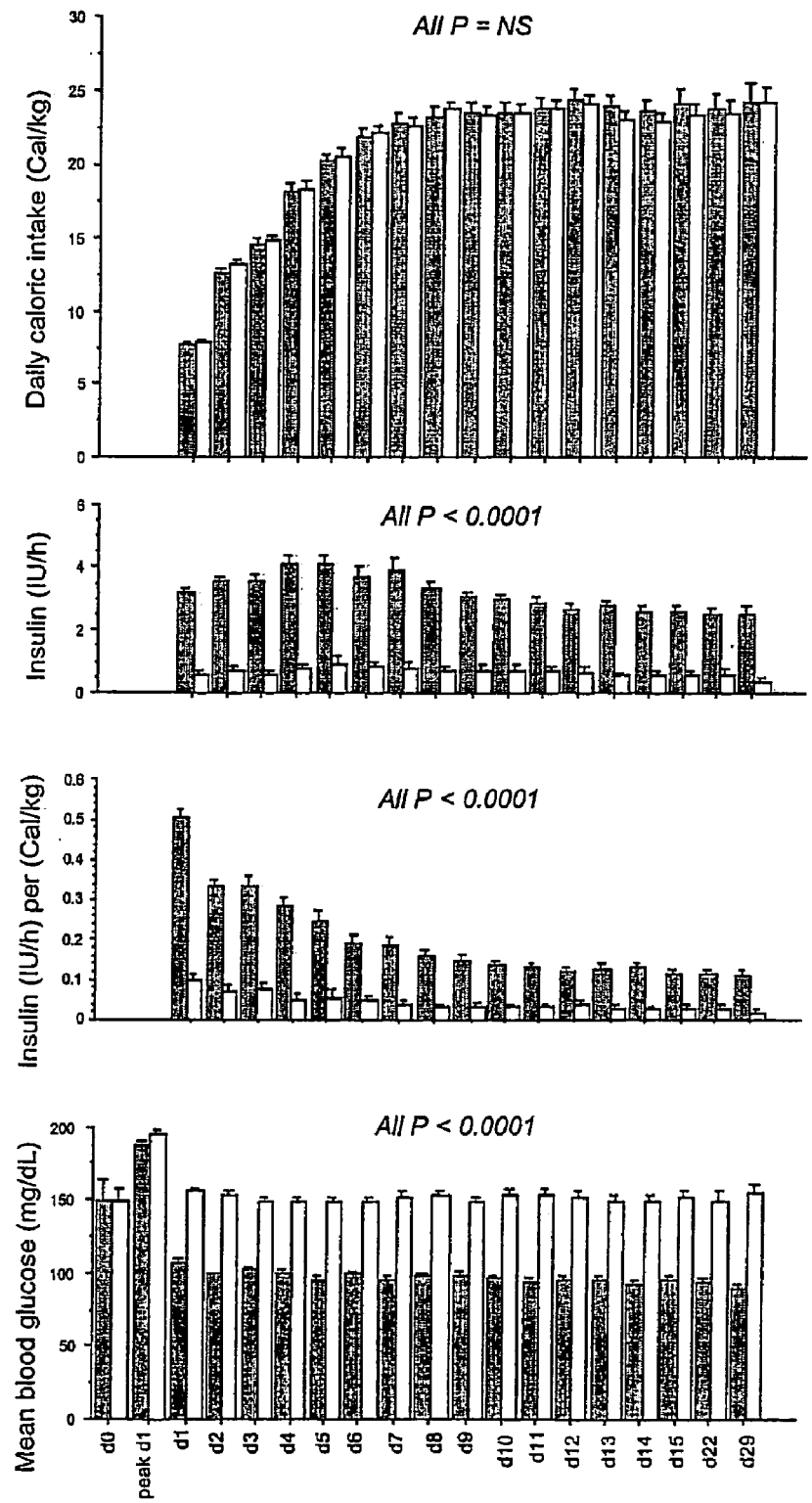
FIG. 1.

Daily caloric intake (Calories per day and kg body weight—top panel), insulin requirements [insulin dose per day expressed as mean amount of units per hour (panel 2); insulin dose per hour corrected for caloric intake per kg body weight (panel 3)] and mean blood glucose levels [including the upon admission blood glucose level (d0) and the highest blood glucose level reached during the first 24 h in ICU (peak d1)—bottom panel] for the first 4 weeks in ICU.

Filled bars represent patients receiving intensive insulin therapy and open bars the patients receiving conventional therapy. Data represent means±SEM. P-values are obtained by Mann Whitney-U test at the different time points. Caloric intake was increased progressively during the first 7 days, and insulin doses corrected for caloric intake progressively decreased over time in ICU, which for the intensive insulin treated patients, in view of their virtually identical blood glucose levels, indicated a progressively improving insulin resistance and/or endogenous insulin secretion.

FIG. 2.

Mean daily insulin doses (Units per hour) corrected for caloric intake per kg body weight for the different independent upon-admission determinants of outcome (hyperglycemia >200 mg/dl at ICU admission, a history of diabetes, a high BMI and reason for ICU admission) in both study groups (intensive insulin treated patient in black bars; conventionally treated patients in open bars).

The higher insulin requirements to maintain normoglycemia in the transplantation group (P<0.0001 vs. all other groups) were explained at least partially by the concomitant administration of high doses of glucocorticoids. Data are expressed as means±SEM. P-values were obtained using Mann Whitney-U test or ANOVA, when appropriate. ** P<0.0001 and  P=0.005 vs. all other groups.

FIG. 3.

Percent risk of death in ICU, development of critical illness polyneuropathy, bacteremia, inflammation (CRP-level higher than 150 mg/l for more than 3 days), need for more than 2 red cell tansfusions and acute renal failure requiring hemofiltration/dialysis among long-stay (>5 days) patients stratified for mean blood glucose levels. Black-filled bars represent patients with a mean blood glucose level below 110 mg/dl; gray-filled bars represent patients with a mean blood glucose level between 110 mg/dl and 150 mg/dl; open bars represent patients with a mean blood glucose level higher than 150 mg/dl. P-values were obtained using Chi-square-test. * P<0.05;  P<0.01; ** P<0.0001 and indicate the level of significance of the difference between the <110 mg/dl and the 110-150 mg/dl groups.

FIG. 4.

Kaplan-Meier cumulative risk of in-hospital death among long-stay (>5 days in ICU) patients with a mean blood glucose level below 110 mg/dl (squares); with a mean blood glucose level between 110 mg/dl and 150 mg/dl (bullets) and patients with a mean blood glucose level higher than 150 mg/dl (diamonds).

P-value of 0.0009, obtained with Mantel-Cox log-rank test, indicates the significance level of the overall difference among the groups and P-value of 0.026 indicates the significance level of the difference between the <110 mg/dl and the 110-150 mg/dl groups.

FIG. 5.

Schematic representation of the control scheme.

The patient's glycemia is measured by a glucose sensor. The controller calculates the desired insulin infusion flow of the actuator (the pump) such that the amount of administered insulin moves the blood glucose level of the patient to, or keeps it at the desired level (i.e., such that glycemia is stabilized between 80 mg/dl and 110 mg/dl). Note that the control of the insulin pump can be either direct or indirect (i.e., the final decision can still be taken by the medical team). See FIG. 2 for a more detailed description of the controller.

FIG. 6.

Schematic representation of the control system.

The initial patient model is calculated using the patient profile and the on-admission parameters (BMI, prior history of diabetes, reason for ICU admission, APACHE-II on admission, on-admission glycemia, caloric intake on admission, concomitant glucocorticoids on admission).

The measured glycemia ($x_k$) enters the control system and is used in two ways. First it is used, together with the current model parameters and the control history, to update the dynamic patient model. In case of a PID-controller, the updated model is used to recalculate the parameters of the PID-controller. In case of an MPC-controller the model is directly used to formulate a patient specific optimization problem. Secondly, both PID and MPC-controllers then use the measured glycemia to calculate the recommended insulin dose ($u_k$).

Moreover, after the initial phase, the patient model can also be fine tuned using the parameters that can influence the patient dynamics (evolution of caloric intake+route of administration+composition, evolution of medication (e.g., glucocorticoids)+dose, time elapsed since admission on the ICU, evolution of severity of disease score).

FIG. 7.

Principle of an automated model-based insulin controller.

* disturbances: BMI, history of diabetes, reason for ICU admission, severity of illness, on-admission hyperglycemia, caloric intake, time in ICU and concomitant medication (glucocorticoids)

FIG. 8.

Performance (in terms of mean relative prediction error MRPE) of a compact on-line model as a function of prediction horizon and time window (number of measurements used to estimate the model parameters at each time instant) for a biological growth process.

DETAILED DESCRIPTION OF THE PRESENT INVENTION

One embodiment of present invention allows to reduce mortality in critically ill patients (who require intensive care) or the time they stay in the ICU through a software-assisted control of glycemia (concentration of glucose in the blood).

The regulation of blood glucose levels is a complex system controlled by several mechanisms. The secretion of insulin by the beta cells of the pancreas is one of the most important naturally occurring mechanisms in the control of glycemia. In normal circumstances, the pancreas will react to an elevated glycemia (e.g., after a meal—post-prandial secretion of insulin) by a raise of its insulin secretion, increasing the amount of this hormone in the bloodstream. This increase in insulin concentrations, in its turn, stimulates the consumption of glucose in the target tissues. This limits the elevation of the blood glucose levels which, after an initial increase, will again reach their fasting levels.

This (natural) control system can be disturbed by an absolute or relative shortage of insulin (causing hyperglycemia or an increased glycemia). In these cases Diabetes Mellitus can be present. In type I diabetes there is an absolute shortage of insulin caused by an immune-mediated destruction of the beta cells. In type II diabetes there is a relative shortage of insulin caused by a lower insulin sensitivity in the target tissues (also called insulin resistance—occurring in somewhat older, obese persons but also during stress—see further) and by abnormal insulin secretion.

Administration of insulin will, in many cases, be the main therapeutic intervention. It was however generally known that insulin resistance and associated hyperglycemia are common in critically ill patients requiring intensive care (including mechanical ventilation) mostly after major surgery (even if they did not have diabetes before). In the past, this was ignored because it was believed that hyperglycemia was a beneficial reaction to stress (Van den Berghe G et al. N Engl J Med 2001; 345: 1359-1367).

However, recently it was showed that normalization of glycemia (between 80 and 110 mg/dl=normoglycemia), through a rigorous administration of insulin, resulted in a spectacular reduction in mortality (e.g., the number of deaths in patients who required intensive care for more than five days was reduced from 20.2% to 10.6%. For the moment, the administration of insulin in intensive care patients is controlled by a labor intensive (considerable workload for the nurses) and empirical protocol (in which a certain degree of freedom is still given—human experience plays an important role). The protocol now requires that blood glucose levels are measured every four hours (or more frequently, especially in the initial phase or after complications). The flow of the continuous insulin infusion is then adjusted using a certain schedule ('Intensive insulin therapy in the critically ill').

A titration algorithms has now been developed by present invention with determinants of insulin requirements and impact of insulin dose versus glycemic control on outcome benefits.

This protocol for obtaining and maintaining normoglycemia, preferably a glycemia below 110 mg/dl and above 80 mg/dl, takes into account the following complicating factors:

- Caloric intake (number of calories, class (proportion of carbohydrates, proteins and fat) and daily interruption of caloric intake) which have been found to have a profound impact on the insulin requirements.
- Switch from intravenous glucose infusion to total parenteral feeding (also intravenously given) and finally to enteral feeding which can profoundly change the dynamics of the process (here the patients are presented as an abstract process with inputs (e.g., administration of insulin) and outputs (e.g., glycemia)).
- the substancial difference between the purpose of the initial phase and the stable or complication phase. In the initial phase, the aim is to obtain normoglycemia as soon as possible. In the stable or complication phase the aim is to maintain blood glucose levels preferably between 80 and 110 mg/dl and to take care that acute events (like infections) have minimal impact (prevention of deviation from normoglycemia).
- Administration of drugs (e.g., glucocorticoids) which was found to be a disturbing factor on the blood glucoe levels.

The constitution or profile of the patient which was found to influence the reaction on insulin administration.

Another embodiment of present invention is a control system that adapts the flow of the insulin infusion using the measurements of the blood glucose levels. This system can (continuously or discontinuously) advise the medical team (physicians or nurses) about the desired insulin administration rate or can, after further validation, apply a more automatic control FIG. 5).

Preferably this control system has the following properties:
1. In the initial phase, hyperglycemia is reduced, as quickly as possible, to stable normoglycemia without causing hypoglycemia.
2. It is robust (i.e., the blood glucose level must be as stable as possible) against complicating factors (some of these factors can possibly be regarded as inputs of the process, like the caloric intake or the administration of glucose).

The actual implementation of this control system for clinical use is a considerably reduction of the efforts necessary to optimize glycemia.

The control system of present invention can be used for patients in the critical care unit, in the coronary care unit, medical intensive care units or during and after surgical or obstetric procedures. This control system can comprise computer-assisted insulin administration, eventually through a subcutaneous insulin pump.

Date of the present invention it is clear that the control system of present that adapts the flow of the insulin infusion can be even used for patients in less critical wards but subjected to insulin resistance and/or increased overall insulin turnover for instance for a subject with obesity disorder. An embodiment of present invention can thus be a computer-assisted insulin administration, eventually through a continuous subcutaneous insulin pump, in a subject confronted with a requirement of inappropriately high levels of insulin for maintaining glucose homeostasis and disproportionate increase in glucose turnover due to a condition of stress or multi-factorial diseases through a continuous subcutaneous insulin pump for control of blood glucose levels at home.

In one embodiment of present control system the blood glucose levels are sampled manually. In second embodiment the blood glucose levels are measured by electrochemical sensors, with sampling times in the order of magnitude of minutes for electrochemical sensors instead of hours as for blood sample measurements.

The model of present invention predicts blood glucose levels given the insulin administration rate and potential disturbances. The model approximates the dynamic behavior of the process for instance the significant time delays can occur between the administration of insulin and its effect on glycemia and the hard constraints on inputs and outputs which are possible, for instance a maximum rate of insulin administration.

Preferably this model has different functions depending on the control structure choice, and its complexity depends on its necessary accuracy.

DESCRIPTION OF THE ILLUSTRATIVE EMBODIMENT

EXAMPLE 1

Material and Methods:

Study Population & Study Design

The study population (mechanically ventilated adults admitted to our predominantly surgical ICU over a one year episode), has been described in detail elsewhere (Van den Berghe G, et al. N Engl J Med. 2001; 345: 1359-1367). Informed consent had been obtained from the closest family member upon ICU admission. The study protocol was approved by the Institutional Ethical Review Board.

A study design has been used as described in detail in Van den Berghe G, et al. N Engl J Med. 2001; 345: 1359-1367, Van den Berghe G, et al N Engl J Med. 2001; 346). At intensive care admission, all patients were started on partial nutritional support with intravenous glucose (200 to 300 g/24 h) and from the next day onward with a standardised feeding schedule with the intention to administer 20 to 30 non-protein Calories/kg/24 h with a balanced composition (0.13 to 0.26 g nitrogen/kg/24 h and 20 to 40 percent of non-protein Calories as lipids) (Ortiz A, et al. J Invest Med. 1997; 45: 50-56) of total parenteral, combined parenteral/enteral or full enteral feeding (Table 1). Enteral feeding was attempted as early as possible, at the discretion of the attending physician.

Upon ICU admission, patients were randomly assigned to either intensive or conventional insulin treatment. Assignment to treatment groups was done by blinded envelopes, stratified according to type of critical illness [(1) cardiac surgery, (2) neurological disease, isolated cerebral trauma or brain surgery, (3) thoracic surgery and/or respiratory insufficiency, (4) abdominal surgery and/or peritonitis, (5) vascular surgery, (6) multiple trauma and severe burns, (7) transplantation, and (8) others] and balanced with the use of permuted blocks of ten.

Adjustment of the insulin dose was based on measurement of whole blood glucose in undiluted arterial blood every one- to four-hours with the use of a glucose analyzer (ABL700, Radiometer Medical A/S, Copenhagen—the coefficient of variation was 2.84% at 90 mg/dl and 3.57% at 220 mg/dl). The dose was adjusted according to a titration algorithm, as stipulated below, by the intensive care nurses, supervised by a study physician who was not involved in the clinical care of the patients.

Insulin Titration

General Aspects

It was advised to consider the titration algorithms as directives that required integration of the guidelines with several patient- and disease-specific aspects such as obesity; pre-existing type I or type II diabetes; type and severity of critical illness; caloric intake, concomitant or intercurrent infections or other complications, the concomitant administration of drugs affecting insulin sensitivity such as glucocorticoids.

Insulin Infusion
  Insulin was given exclusively by continuous intravenous infusion through a central venous line using a 50 mL syringe driven pump (Perfusor-FM® pump; B. Braun, Melsungen, Germany). The standard concentration was 50 IU Actrapid HM® (Novo Nordisk Denmark) in 50 ml NaCl-0.9%.
  Prepared solutions, stable for up to 24 h when kept below 25° C., were not to be used beyond that time.

Measurement of Blood Glucose Levels
  Whole blood glucose levels were measured in undiluted arterial blood. Undiluted samples were obtained by removing at least 4 times the flush-volume in the arterial line between the sampling point and the arterial puncture site before the actual sample was taken.
  During the first 12 to 24 h after admission to ICU, until the targeted range of blood glucose level was reached, one- to two-hourly measurement of blood glucose was advised. Thereafter, blood glucose was measured every 4 hours, unless steep falls or rises in blood glucose level occurred, for which hourly control after each dose adjustment was advised.

Special Concerns Regarding Alterations in Caloric Intake

Attention was drawn to always assure adequate administration of the prescribed nutrients.

In order to avoid fluctuating blood glucose levels and too frequent need for re-adjustment of the insulin dose, IV glucose-containing solutions were always administered by infusion pump.

At the time of planned interruptions of feeding, the insulin dose was reduced proportionately in order to avoid hypoglycemia. Hence, in a patient on total enteral nutrition, insulin was virtually stopped during the twice daily 2 h interruptions of tube feeding. In some patients, however, including those who were suffering from diabetes and requiring insulin before ICU admission, a low maintenance dose was needed during that time.

At the time of patient transportation to an investigation or to the operating room for surgery, all IV and enteral administration of feeding was usually stopped and insulin infusion was temporarily discontinued. Blood glucose level was measured to ensure an adequate level before transport.

Whenever a patient was extubated and assumed to re-start (limited) oral food intake, the IV or tube feeding was usually reduced in order to allow appetite to re-occur. The insulin dose was proportionately reduced, often temporarily discontinued.

Special Concerns About Concomitant Drugs

When glucocorticoids were given in high doses (>90 mg/d hydrocortisone or its equivalent), insulin dose was increased to overcome the associated insulin resistance. The total daily dose of glucocorticoids was administered as a continuous infusion to avoid fluctuating insulin requirements occurring with intermittent bolus injections.

Special Concerns in a Patient at Risk for Acute Renal Failure in Whom an Hourly Substitution of Urinary Fluid Loss was Applied to Avoid Fluctuating Intravascular Filling Status In order to co-adjust insulin dose with the variable amounts of glucose containing solutions (glucose 5%, glucose 3.3% or glucose 2.5%) infused to substitute the variable hourly urine output, 16, 12 or 10 IU insulin per liter of substitution fluid, respectively, were added to the infusion bag. This insulin administration was additional to the hourly dose, which was given separately by infusion pump.

Insuline Therapy and Study Objectives

Intensive Insulin Therapy:

Starting of Insulin Infusion and Initial Stabilisation of Blood Glucose Level

When blood glucose level exceeded 110 mg/dl (6.1 mmol/l), insulin was started at 2 IU/h (4 IU/h if first blood glucose level exceeded 220 mg/dl).

When next blood glucose was >140 mg/dl, insulin dose was increased by 2 IU/h.

When next blood glucose level was 110-140 mg/dl, insulin was increased by 1 IU/h.

When blood glucose approached 80-110 mg/dl, insulin was adjusted by 0.1-0.5 IU/h.

When blood glucose level was 80-110 mg/dl, insulin dose was unaltered.

Dose Adjustments After Initial Stabilisation

Dose adjustments were proportionate to the observed change in blood glucose. When blood glucose decreased by >50%, dose was reduced to half and blood glucose level checked within the next hour.

When blood glucose was 60-80 mg/dl, insulin was reduced depending on the previous blood glucose level and blood glucose level checked within the next hour.

When blood glucose was 40-60 mg/dl, insulin infusion was stopped, adequate baseline glucose intake was assured and blood glucose level checked within the next hour.

When blood glucose was <40 mg/dl, insulin infusion was stopped, adequate baseline glucose intake was assured, glucose was administered per 10 g IV boluses and blood glucose level checked within the next hour.

When blood glucose started to decrease within the normal range in a stable patient, recovery of insulin sensitivity was assumed and insulin dose reduced by 20%.

Additional blood glucose controls were advised when changes in body temperature and/or infection occurred.

At discharge from ICU, a less strict approach was adopted (glycemia≦200 mg/dL) in order to avoid hypoglycemia in the less well controlled setting of a regular ward. When a (previously non-insulin requiring) patient was normoglycemic on <2 IU/h insulin, the insulin infusion was stopped. Blood glucose level before discharge was targeted below 200 mg/dL. When insulin was required to maintain blood glucose level below 200 mg/dL, the patient was presumed to have pre-existing diabetes and follow up by an endocrinologist was planned.

Conventional Insulin Therapy

Starting Up and Dose Adjustment of Insulin Infusion

As soon as blood glucose level exceeded 215 mg/dL (12 mmol/L), insulin infusion was initiated at a starting dose of 1 IU/h.

When a control blood glucose level was >200 mg/dL, insulin dose was increased by increments of 1 IU/h Once blood glucose level was between 180 and 200 mg/dl, insulin dose was kept constant When blood glucose level decreased below 180 mg/dL, insulin infusion was decreased until blood glucose level was between 180-200 mg/dl. Insulin dose was further decreased and eventually completely stopped when blood glucose levels decreased further. Insulin infusion was only re-started when blood glucose exceeded 215 mg/dl.

Study Objectives

The primary clinical results of this study, which involved 1548 patients (783 treated conventionally and 765 treated with intensive insulin therapy), were published previously (Van den Berghe G, et al; N Engl J Med. 2001; 345: 1359-1367). The aims of the current analysis were:

(1) to report on feasibility and safety of intensive insulin therapy in the ICU by providing details of feeding strategy, insulin requirements and blood glucose control over time (2) to statistically define the factors that independently determine insulin requirements (3) to analyse the separate impact of glycemic control and amount of exogenous insulin infused on mortality and morbidity outcome measures (development of critical illness polyneuropathy as diagnosed by blinded weekly systematic EMG screenings, acute renal failure requiring dialysis, bacteremia, prolonged inflammatory responses as defined by C-reactive protein (CRP)-level>150 mg/l for more than 3 days) and transfusion requirements.

(4) to study the impact on outcome measures of strict normoglycemia (<110 mg/dl) compared with an intermediate level of blood glucose control (110-150 mg/dl) among long-stay patients.

Statistical Analysis

Data are presented as means±SEM or medians ($25^{th}$ to $75^{th}$ percentile) unless indicated otherwise.

Difference between study groups were analysed by Chi-square test, unpaired Student's t-test, Mann Whitney-U test and Mantel-Cox log-rank test, when appropriate. Multivariate logistic regression analysis was performed to assess the impact of blood glucose level versus insulin dose on the observed outcome benefits. After univariate simple regression analysis, stepwise forward and backward regression analysis was done to define the independent determinants of the insulin dose required to maintain normoglycemia. P-values below 0.05 were construed significant.

EXAMPLE 2

Results

Detailed Description of Daily Caloric Intake, Insulin Doses and Blood Glucose Control Over Time in Conventionally Treated Patients and in Patients Receiving Intensive Insulin Therapy Daily caloric intake, insulin requirements and blood glucose levels (including the upon admission blood glucose level and the highest blood glucose level reached during the first 24 h in ICU) are depicted in FIG. 1.

All patients underwent a gradual transition from intravenous glucose infusion upon ICU admission to normocaloric balanced nutrition comprising glucose, proteins and lipids, preferably administered via the enteral route. Hence, daily caloric intake progressively increased until ICU day 7, equally in both study groups, starting from a mean 8 Cal/kg/day and reaching a mean 24 Cal/kg/day (FIG. 1, first panel). This strategy resulted in comparable amounts of calories, glucose, proteins and lipids in both study groups at all times, a prerequisite for attributing observations to intensive insulin therapy.

Of all patients in ICU for >5 days (N=451), the group among whom intensive insulin therapy reduced mortality, 60% (N=267) received combined parenteral-enteral feeding with up to a mean 68% of nutrients administered enterally. After 7 days ICU, 85% of the patients received at least partial enteral nutrition. Intensive insulin therapy was equally effective whether or not patients received enteral feeding in ICU: mortality was reduced from 18.8% to 10.2% (P<0.05) in the group in ICU for >5 days and receiving combined parenteral-enteral feeding, and from 22.3% to 11.1% (P<0.05) in the parenterally fed only group. Effects on morbidity were equally independent of feeding regimen.

With the nutritional strategy applied, 99% of patients in the intensive insulin group required exogenous insulin to maintain mean blood glucose levels at (mean±SEM) 103±1 mg/dl. In the conventionally treated group, only 39% of patients revealed blood glucose levels peaking over 215 mg/dl and thus required exogenous insulin. Mean blood glucose level for the entire conventionally treated group therefore was 153±1 mg/dl and 173±2 mg/dl for the subgroup requiring insulin. In both study groups, targeted ranges of blood glucose were reached within 24 h of intensive care.

Mean±SEM insulin dose per day was 68±2 units in the patients randomized to receive intensive insulin therapy (70±2 units per day in the patients actually receiving insulin) and 12±1 units per day in the conventionally treated patients (41±3 units per day in the patients actually receiving insulin). The mean hourly doses on a daily basis are depicted in FIG. 1, second panel. Insulin requirements in order to reach normoglycemia were highest and most variable during the first 6 hours after admission (mean 7 units per hour, in 10% of the patients more than 20 units per hour). Normoglycemia was reached within 24 h with, for a 70 kg patient, a mean 77 units per day for a mean 550 Calories on the first day and 94 units per day on ICU day 7 when full nutrition was given (a mean 1600 Calories). After day 7, caloric intake remained constant though insulin doses decreased by 40% from day 7 to day 12, remaining stable thereafter. At all times, the within-patient variability of the insulin dose remained within a mean 75% (95% confidence interval of 25% to 125%) of the insulin dose on day 1.

In 0.8% of conventionally treated patients and 5.2% of intensive insulin treated patients (P<0.0001), hypoglycemia (<40 md/dl) occurred after a median 11 (IQR 2-20) and 6 (2-14) days, respectively (P=0.6). In 18% of the intensive insulin treated patients who encountered hypoglycemia, such an event occurred at more than one [median 3 (IQR 2-4)] occasion. More than one hypoglycemic event did not occur in conventionally treated patients. Of all episodes of hypoglycemia, 90% occurred after stable blood glucose levels within the targeted range had been reached and 62% of those occurred in association with interruption of enternal feeding, which was inadvertently done without adequately reducing the insulin dose. Because of the frequent insulin dose adjustments, particularly when blood glucose levels dropped steeply, hypoglycemia episodes were always brief and serious complications, such as hemodynamic deteriorations, convulsions or permanent consequences, did not occur.

Factors Determining Insulin Requirements

Figure 2:
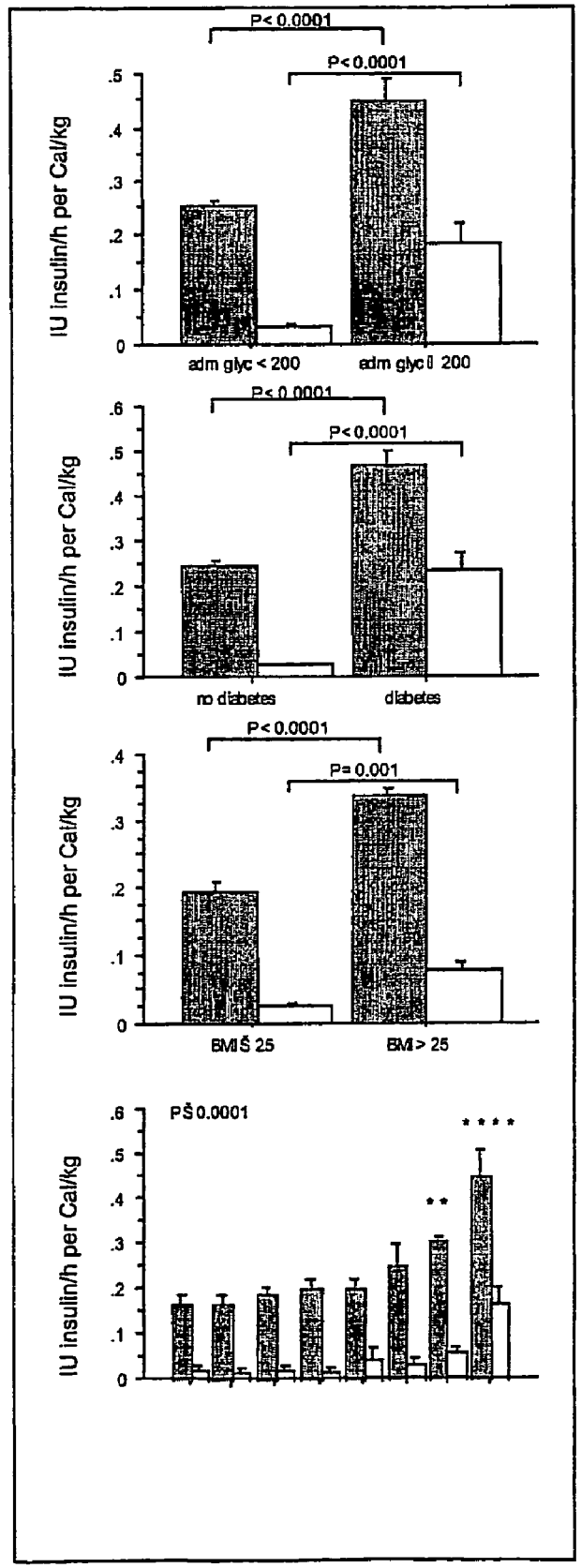

On univariate analysis, the factors significantly correlated with hourly insulin dose required to maintain normoglycemia were BMI (R=0.34), history of diabetes (Rho=0.50), reason for ICU admission (Rho=0.08), APACHE-II on admission (Rho=0.10), blood glucose level on admission (R=0.34), mean daily caloric intake (R=0.23), concomitant treatment with glucocorticoids (Rho=0.37), and time in ICU (R=−0.14) (FIG. 1 and FIG. 2). Stepwise regression analysis revealed that they were all independent determinants, except for APACHE-II score (Souba W W. Et al. N Engl J Med. 1997; 336: 41-48) (positively correlated with on-admission glycemia; Rho=0.14; P<0.0001) and concomitant treatment with glucocorticoids (related to reason for ICU admission: more than 86% of the transplanted patients received glucocorticoids versus 24-30% among all other patient groups; P<0.0001). Taken together, the independent factors (in order of impact: history of diabetes, BMI, blood glucose level on admission, caloric intake, time in ICU and reason for ICU admission) explained 36% of the variability in mean hourly insulin requirements to maintain normoglycemia.

Caloric intake, an independent determinant of insulin dose required to maintain normoglycemia, varied according to the type of illness (more calories were given to vascular surgery patients, brain surgery or cerebral trauma patients and multiple trauma patients compared with other subgroups) and with time in ICU (FIG. 1, first panel). Hence, assessment of differences in insulin requirement to maintain the preset glycemic range with time in ICU (FIG. 1, third panel) and among the different patient groups (FIG. 2) was done by comparing the ratio of hourly insulin dose (IU/h) over caloric intake (Cal/kg BW/24 h). In the intensive insulin treated patients, in whom blood glucose levels were tightly "clamped" between 80-110 mg/dL and hence virtually similar at all times, this ratio of insulin dose over caloric intake is also a surrogate marker of insulin resistance. In both study groups, this ratio continued to decrease significantly over time (P<0.0001) (FIG. 1, third panel).

Among patients in ICU for more than 5 days, the route of feeding determined this ratio: the insulin dose required to maintain normoglycemia, corrected for caloric intake per kg body weight, was a median 26% higher in exclusively parenterally fed patients compared with those receiving at least some enteral nutrition (P=0.007).

Figure 3:
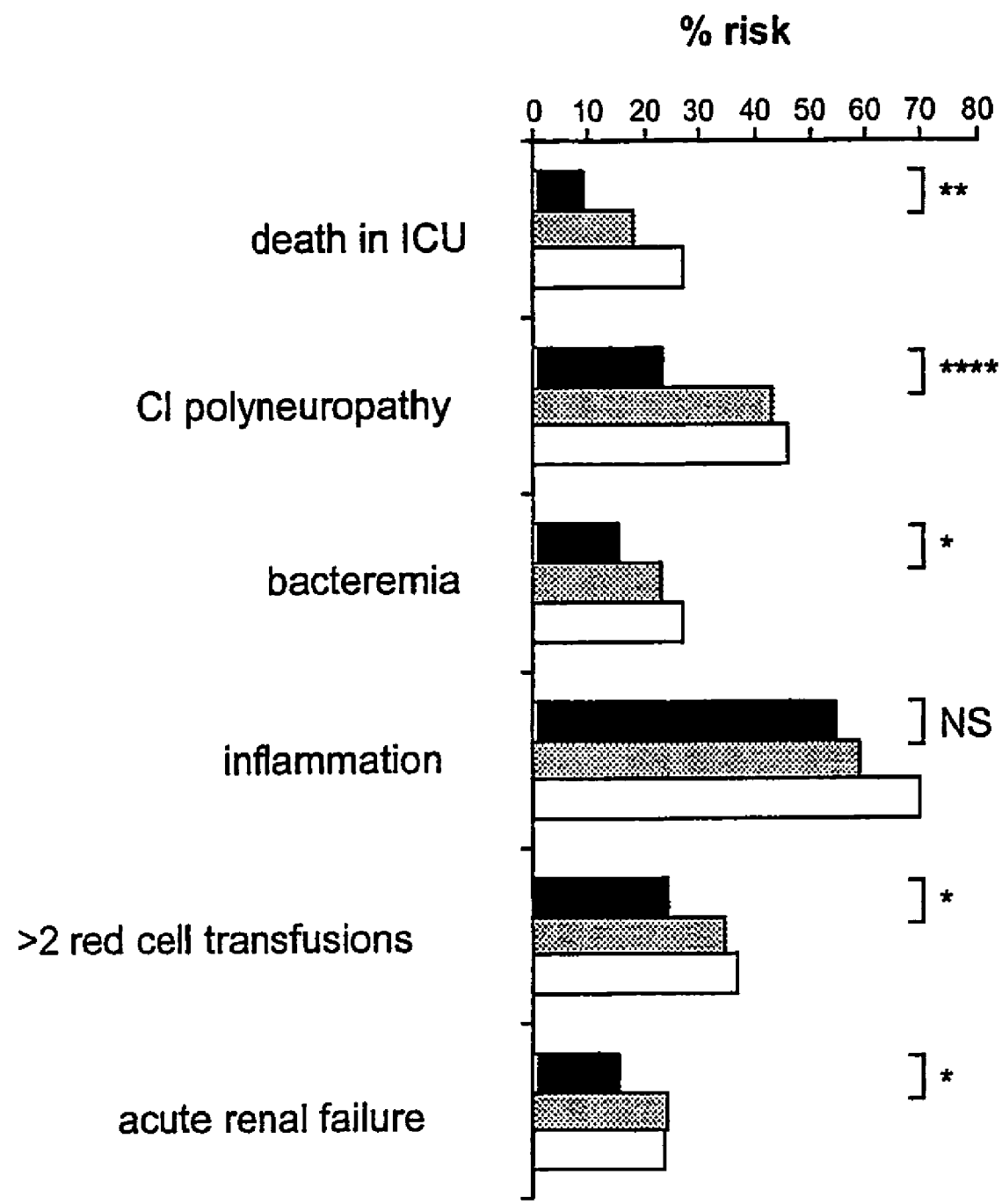
Figure 4:
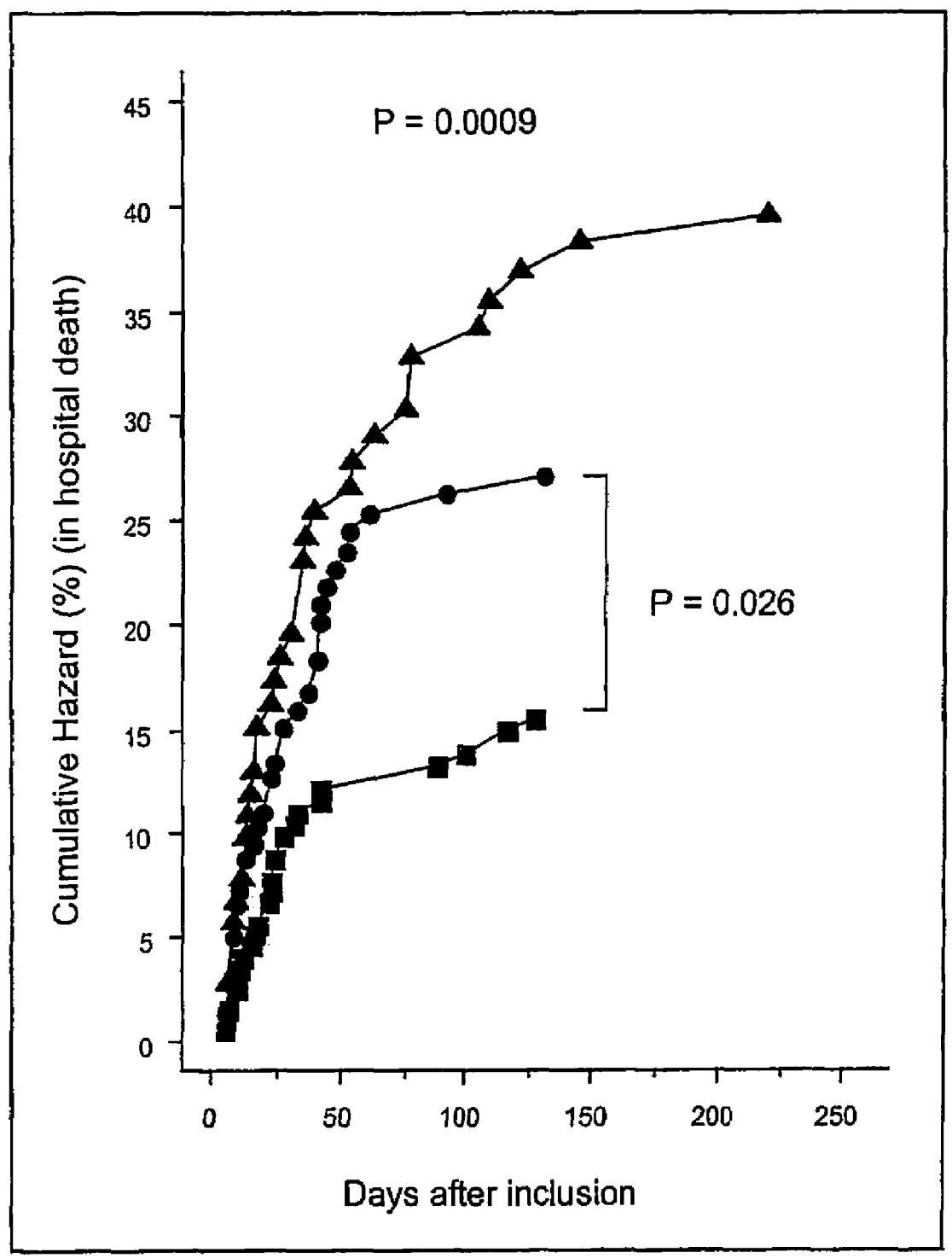

Analysis of the Impact of Actual Glycemic Control Versus Mean Amount of Infused Insulin on Mortality and Morbidity (Table 1, 2 and FIGS. 3, 4).

For the entire study group, the mean daily insulin dose and the mean blood glucose level were entered into a multivariate logistic regression model together with all other univariate determinants of adverse outcome (age, delayed ICU admission, on-admission APACHE-II score, reason for ICU admission, history of malignancy and diabetes, on-admission hyperglycemia) (McCowen K K et al. Crit. Care Clin 2001; 17: 107-124; O'Niel D. A. et al Stroke 1991, 22: 842-847; Capes S E, et al. Lancet 2000; 355: 773-778). For ICU mortality (Table 1), both the mean daily amount of infused insulin (P=0.005) and the mean level of blood glucose during ICU stay (P<0.0001) were independent positive risk factors. For critical illness polyneuropathy (P<0.0001), bacteremia (P=0.02) and need for red cell transfusion (P=0.06) (Table 2), only the mean level of blood glucose during ICU stay, and not the insulin dose, appeared to be an independent risk factor. For the occurrence of prolonged inflammation (defined as more than 3 days CRP level above 150 mg/l), the insulin dose (P=0.02) and the level of blood glucose (P=0.0006) were independent positive risk factors. In contrast, for acute renal failure and the need for renal replacement therapy, not the actual level of blood glucose but the dose of insulin was an independent negative predictor (P=0.03).

Among the long-stay patients (ICU stay>5 days), the group among which intensive insulin therapy reduced mortality and morbidity, there was a gradual decrease in risk of ICU (FIG. 3) and hospital death (FIG. 4) with decreasing blood glucose levels (<110 mg/dl; 110-150 mg/dl; >150 mg/dl) without an identifiable threshold below which no further risk reduction occurred. Also for the occurrence of critical illness polyneuropathy, bacteremia, need for red cell transfusion and acute renal failure, the risk was lower among patients with maintained strict normoglycemia compared with patients in whom the blood glucose level was moderately elevated (110-150 mg/dl). There was no indentifiable threshold blood glucose level below which no further reduction of risk of these complications occurred (FIG. 3). In contrast, for prevention of prolonged inflammation, as defined by a CRP-level of >150 mg/l for >3 days, the threshold blood glucose level may be higher than 110 mg/dl (FIG. 3).

Discussion

Strict maintenance of normoglycemia with intensive insulin therapy has shown to reduce intensive care and hospital mortality and morbidity of critically ill adult patients in a surgical ICU (Van den Berghe G, et al. N Engl J Med. 2001; 345: 1359-1367). We here report that lowering of blood glucose, achieved with insulin titration according to a simple algorithm, rather than the actual amount of insulin given was most significantly related to the observed reduction in mortality, critical illness polyneuropathy, bacteremia, inflammation and anemia but not to the prevention of acute renal failure, for which the insulin dose was an independent determinant.

Normoglycemia could be effectively and safely reached within 24 h after ICU admission and maintained throughout ICU stay by medically-supervised, nurse-controlled insulin titration, guided by a simple titration algorithm. A few on-admission patient- and disease-related factors (BMI, history of diabetes, reason for ICU admission, on-admission hyperglycemia) (McCowen K C, et al. Crit Care Clin. 2001; 17: 107-124, O'Neill P A, et al. Stroke. 1991; 22: 842-847, Knaus W A, et al. Crit Care Med. 1985; 13: 818-829; Capes S. E. et al. Lancet 2000; 355: 773-778), the mean daily amount of calories per kg body weight, the time in ICU and concomitant medication such as glucocorticoids, were able to predict insulin requirements for 36%. This indicates that 64% of the insulin dose adjustments were not predictable by the studied variables and thus were based on the frequently measured blood glucose levels and empirically guided by factors such as the time course of the previous changes in blood glucose level, an eventual rise in body temperature and intercurrent infections, as advised in the insulin titration guidelines. Episodes of hypoglycemia occurred infrequently, although more often with intensive insulin therapy than with conventional insulin therapy. Hypoglycemic episodes were never accompanied by serious adverse events because the algorithm guaranteed quick detection and correction. Hypoglycemia occurred in the stable phase and was mostly attributable to human error such as inadequate insulin dose reduction during interruption of enteral feeding. After implementation of intensive insulin therapy as part of routine clinical patient care in our ICU, these errors appeared avoidable with progressively increasing experience of the nursing team. Targeting the blood glucose control so strictly below 110 mg/dl appeared necessary to optimally prevent ICU and in-hospital deaths, critical illness polyneuropathy, bacteremia, anemia and acute renal failure, as even moderate hyperglycemia (110-150 mg/dl) was associated with higher risk of these complications. Hence the higher risk of brief hypoglycemia was clearly outweighed by the observed benefits of intensive insulin therapy.

In the studied population who received progressively increasing amounts of nutritional support, from a mean 550 Cal to a mean 1600 Cal over the first 7 days of intensive care administered via the parenteral and/or enteral route, the lowering of blood glucose rather than the amount of infused insulin which was related to the observed benefits of the intervention, as indicated by the multivariate logistic regression analysis. Although the study was not specifically designed to evaluate the separate impact of infused insulin and of metabolic control, these results point to an important role of the latter. Indeed, although direct effects of insulin such as anti-inflammatory effects through suppression of cytokine production or signalling (Dandona P. J. Clin. Endocrinol. Metabl. 2001, 86: 3257-3265) or anabolic effects (Ferrando A A, et al. Ann Surg 1999; 229: 11-18) may have played a role, favorable effects mediated specifically by the prevention of hyperglycemia appear to have dominated. Examples of the latter are improvement of coagulation and fibrinolysis (Carr M E. J Diabetes Complications 2001; 15: 44-54) and of macrophage function (Kwoun M O, et al. J Parent Enteral Nutr. 1997; 21: 91-95), acting alone or together. Whether the lowering of the blood glucose was the primary effector or rather a simple reflection of other metabolic effects of intensive insulin therapy, such as improved clearance and hence less toxicity of circulating fatty acids, remains unclear.

The results also indicate that the observed benefits of our strategy to maintain normoglycemia with insulin (average 0.04 IU/kg/h) during normal intake of glucose (9 g/h) and calories (mean 19 Cal/kg/day) probably differ from those of "glucose-insulin-potassium" (GIK) solutions, used for improvement of cardiac performance during and after myocardial injury (Svensson S, et al. J Thorac Cardiovasc Surg. 1990; 99: 1063-1073; Fath-Ordoubadi F, et al; Circulation 1997; 96: 1152-1156, 23). The goal of GIK infusions is to stimulate myocardial metabolization of glucose instead of fatty acids when oxygen supply is compromized. Hence, GIK solutions include a much higher dose of both insulin (ranging from 0.1 to 1 IU/kg/h depending on the protocol used) and glucose (ranging from 30 to 80 g/h) than what we provided, and, most importantly, these solutions are infused without targeting normoglycemia. In fact, most studies on GIK have reported substantial hyperglycemia. We found that it was a low level of blood glucose, rather than a high insulin dose, which apparently protected against most ICU complications and death, without an identifiable threshold, below which no further risk reduction occurred. For prevention of prolonged inflammatory responses, defined as CRP levels higher than 150 mgA for more than 3 days, during critical illness, however, blood glucose levels somewhat higher than 110 mg/dl may still be effective.

The prevention of acute renal failure, for which the insulin dose was an independent determinant, appeared a notable exception. This observation may either point to a direct protective effect of insulin on the kidney or to the fact that insulin is to a large extent cleared through the kidney (Rabkin R, et al. N Engl J Med. 1970; 282: 182-187), which may reduce the need for exogenous insulin in patients with acute renal failure. Alternatively, the lower insulin requirements to maintain normoglycemia in patients on hemofiltration can also be explained by the fact that hemofiltration clears glucose from the blood proportionately to the hemofiltration volume and thus to a much greater extent than does the normal kidney.

Insulin requirements, particularly when corrected for body weight and caloric intake, decreased steadily with time in ICU. Insulin doses needed to obtain normoglycemia were highest and varied substantially among patients during the first 6 hours after ICU admission. Within the first 24 hours, normoglycemia was reached with on average, for a 70 kg patient, 70 units of insulin per 500 Calories. Maintenance of normoglycemia was achieved with insulin doses progressively decreasing to about 20 units per 500 Calories on day 7 of intensive care. Besides this progressively decreasing insulin requirement, within-patient insulin dose variations remained limited. Since the majority (87%) of the patients were not previously diabetic, and since blood glucose levels in the intensive insulin group were indeed adequately clamped around 100 mg/dl from day 1 until the last day in ICU, the decreasing insulin requirements with time in ICU reflect several fold improvement of either insulin resistance and/or endogenous insulin production.

We observed a 26% higher insulin requirement to maintain normoglycemia for identical amounts of calories in patients who received exclusively parenteral feeding compared with those who received enteral nutrition. This can be explained by the incretin effects on insulin secretion with enteral feeding in non-diabetic subjects (Kieffer T J, Habener J F. Endocr Rev. 1999; 20: 876-913). Furthermore, endogenous insulin released by enteral feeding is likely to induce more pronounced suppression of hepatic gluconeogenesis and more hepatic glucose uptake than peripherally infused insulin (Zucker G J, et al. Diabetes. 1997; 46: 372-378).

The higher insulin requirements to obtain nonmoglycemia in patients fed with parenteral compared with enteral feeding indicates that parenterally fed patients are more at risk for hyperglycemia. Furthermore, the outcome benefits of intensive insulin therapy were present regardless of the feeding regimen. Hence, our observations have implications for the controversy on early enteral feeding (Braga M, et al. Crit Care Med. 1998; 26: 24-30; Zaloga G P. et al. Crit Care Med. 1999; 27: 259-261). Indeed, some of the reported benefits of early enteral feeding may be explained by the concomitant lower risk of hyperglycemia. Our data suggest that the outcome advantage of early enteral nutrition as compared with parenteral feeding may fade when intensive insulin therapy is given to avoid hyperglycemia.

Normoglycemia was thus safely reached within 24 h and maintained during intensive care by using simple insulin titration guidelines. The lowering of blood glucose levels, or effects reflected by normoglycemia, rather than the amount of infused insulin per se was related to the observed protective effects of intensive insulin therapy on morbidity and mortality.

EXAMPLE 3

In present invention a system has been developed that can advise the medical team about the desired insulin administration rate or can apply a more automatic control.

It has the following properties:
1. In the initial phase (first 24 h) the hyperglycemia is reduced, as quickly as possible, to stable normoglycemia without causing hypoglycemia.
2. The control system is robust (i.e., the blood glucose level is as stable as possible) against complicating factors (e.g., concomitant infection) and changing circumstances (e.g., decreasing insulin resistance, other route of feeding, change in medication, . . . ).

Figure 5:
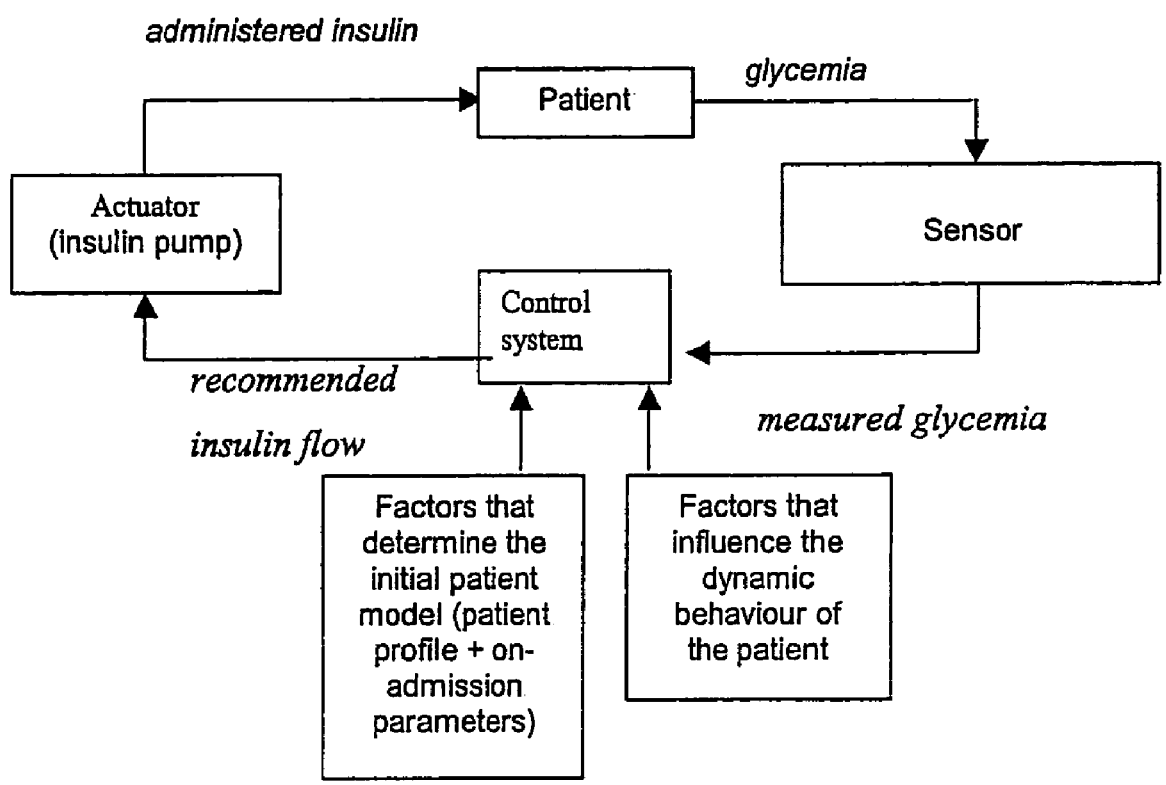
Figure 6:
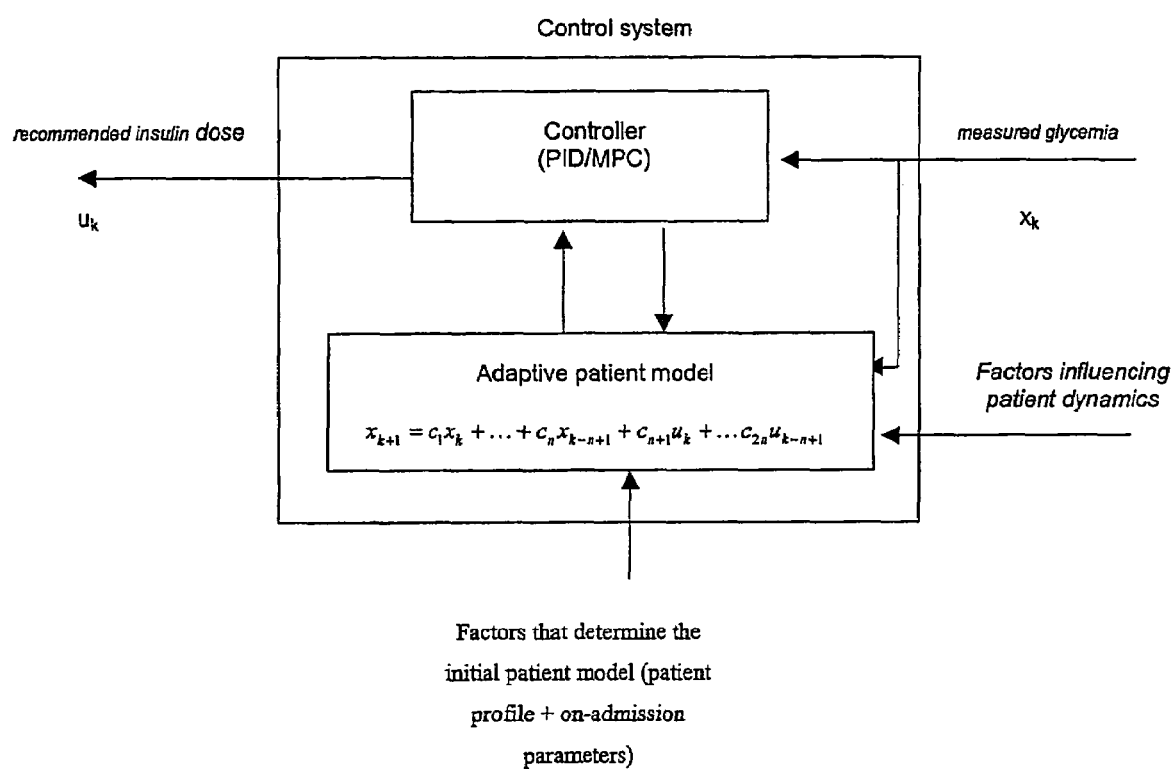

A general overview of the control system can be inspected in FIG. 5. The system consists of three main parts:
1. Sensor: the glycemia is measured by a glucose sensor that uses blood obtained through or present in an arterial line (which is present in most patients in the ICU).
2. The actuator: consists of a programmable insulin pump, which delivers insulin by continuous intravenous infusion through a central venous line. The pump can be programmed manually, based on the insulin dose proposed by the controller. In this configuration the system acts purely as an advising system, whose advice can still be overruled. The programming can also be performed automatically by the controller, using a serial link or an IR link, depending on the specific hospital situation.
3. The control system: this system adapts the insulin infusion levels to the measured glycemia and incorporates two main components (see FIG. 6):
   a. The mathematical (adaptive) model of the patient: in the initial phase an initial model is used based on the 'profile' or 'constitution' of the patient (factors that can influence the basal or mean insulin requirements; this profile can consist of the following variables: BMI, prior history of diabetes, reason for ICU admission) and on-admission parameters (APACHE-II on admission, on-admission glycemia, caloric intake on admission, concomitant glucocorticoids on admission). According to this profile and the on-admission parameters, patients are classified into distinct classes each associated with their own parameter settings for the initial model. After the initial phase, the incoming closed-loop measurements are used to adapt the initial parameters of the model such that it more closely approximates the dynamic behaviour of the glycemia in that particular patient. Moreover, in this phase the model parameters can also be tuned by input data that can influence the dynamic behaviour of the patient (evolution of caloric intake+route of administration+composition, evolution of medication (e.g., glucocorticoids)+dose, time elapsed since admission on the ICU, evolution of severity of disease score). In this way the uncertainty on the parameter estimates can be reduced to improve the controller performance.

A low-order ARX-model is used as patient model:

$$x_{k+1} = c_1 x_k + c_2 x_{k-1} + \ldots + c_n x_{k-n+1} + c_{n+1} u_k + c_{n+2} u_{k-1} + \ldots c_{2n} u_{k-n+1}$$

where $x_k$ is the state of the patient at discrete time k (in this case the blood glucose level), $u_k$ is the input of the patient model at discrete time k (in this case the insulin infusion flow) and $c_i$ are parameters determining the model behaviour. Due to the complex behaviour of ICU-patients and wide variation in patient conditions it is impossible to determine a unique set of parameters $c_i$ describing all possible patients. Therefore, using the patient profile and on-admission parameters, patients are classified into different groups and for each group an optimal set of parameters $c_i$ is determined in function of the above stated factors. This is done by analysing prior patients glucose level and insulin infusion flow measurements and extracting each patients model parameters $c_i$. Using classical statistical techniques it is then possible to calculate the expected values of the $c_i$ and the expected estimation error $\Delta c_i$ for each class given the profile of the patient and the on-addmission parameters.

This way the obtained model more closely resembles the real patients expected behaviour. Similarly, the estimation error $\Delta c_i$ will be smaller compared to the case when none of the above mentioned factors are used. In the controller the estimation error is used to achieve robustness against model uncertainty and thus this reduction of the estimation error $\Delta c_i$ is aimed to keep the control problem feasible and improve its performance.

Alternatively, instead of an ARX-model, a state-space model can also be used to achieve similar results, but this has the drawback that the number of parameters is potentially larger, complicating the statistical analysis.

In another alternative setting, physical understanding of glucose dynamics in the human body can be incorporated in the model to decrease the number of free parameters.

During operation of the controller, the model parameters $c_i$ are updated to represent the dynamics of the patients glucose level. This can e.g. be done in a Bayesian statistical framework, using the initial guess of the parameters as prior knowledge and the measured closed-loop data as new observations. Alternatively, other algorithms (e.g. RLS) for adaptive filtering can be applied.

b. The controller A choice can be made between the use of a PID- or an MPC-controller. The latter increases performance but also increases computational demand on the controller hardware, leading to an increased cost. In both cases the adaptive patient model (see above), along with the calculated uncertainty on the parameter estimates, is used in the control scheme to obtain a robust controller.

In case of a PID-controller (state feedback controller with proportional, integrating and differential component)

$$u = K\left(x + \frac{1}{T_i}\int x \, dt + T_d \frac{dx}{dt}\right),$$

the controller parameters K, $T_i$, $T_d$ are recalculated using the current patient model parameters $c_i$. Since the patient is a stable SISO (Single-Input Single-Ouput) system, this can be done using the classical Ziegler-Nichols method, where K, $T_i$ and $T_d$ are calculated using the following rules $$K = \frac{1.2}{RL}$$

$$T_i = 2L$$

$$T_d = \frac{L}{2}$$

where R and L are parameters determined by the step response of the system. These can thus be calculated directly from the $c_i$ e.g. by online simulation.

Robustness against model uncertainty can be achieved by using the estimated $\Delta c_i$ to calculate the patents worst case response instead of the most likely response.

After updating the K, $T_i$, $T_d$, the controller can be applied directly to calculate the recommended insulin infusion flow. Other existing rules of thumb for the choice of K, $T_i$, $T_d$ can also readily be used instead of the above suggested Ziegler-Nichols method.

In case of an MPC-controller the model is explicitly used to formulate the optimization problem that is solved in each time step to obtain the recommended insulin infusion flow $$\min_{x,u} \left( \sum_{i=1}^{P} x_{k+i}^T Q x_{k+i} + \sum_{i=0}^{P-1} u_{k+i}^T R u_{k+i} \right)$$

subject to $$x_{k+1} = c_1 x_k + \ldots + c_n x_{k-n+1} + c_{n+1} u_k + \ldots c_{2n} u_{k-n+1} \quad k=1 \ldots p$$

where Q, R and P are fixed design parameters of the controller. In this way the control action is automatically adjusted to the adaptive model of the patient.

In each case (PID/MPC), the calculated control action (insulin infusion flow) is recalculated on a regular basis. This sampling time can range from 15 min. to up to 2 hrs., depending on the type of controller selected and the type of interface to the actuator (manual or automatic). This to accommodate the specific hospital situation and demands as good as possible.

EXAMPLE 4

Figure 7:
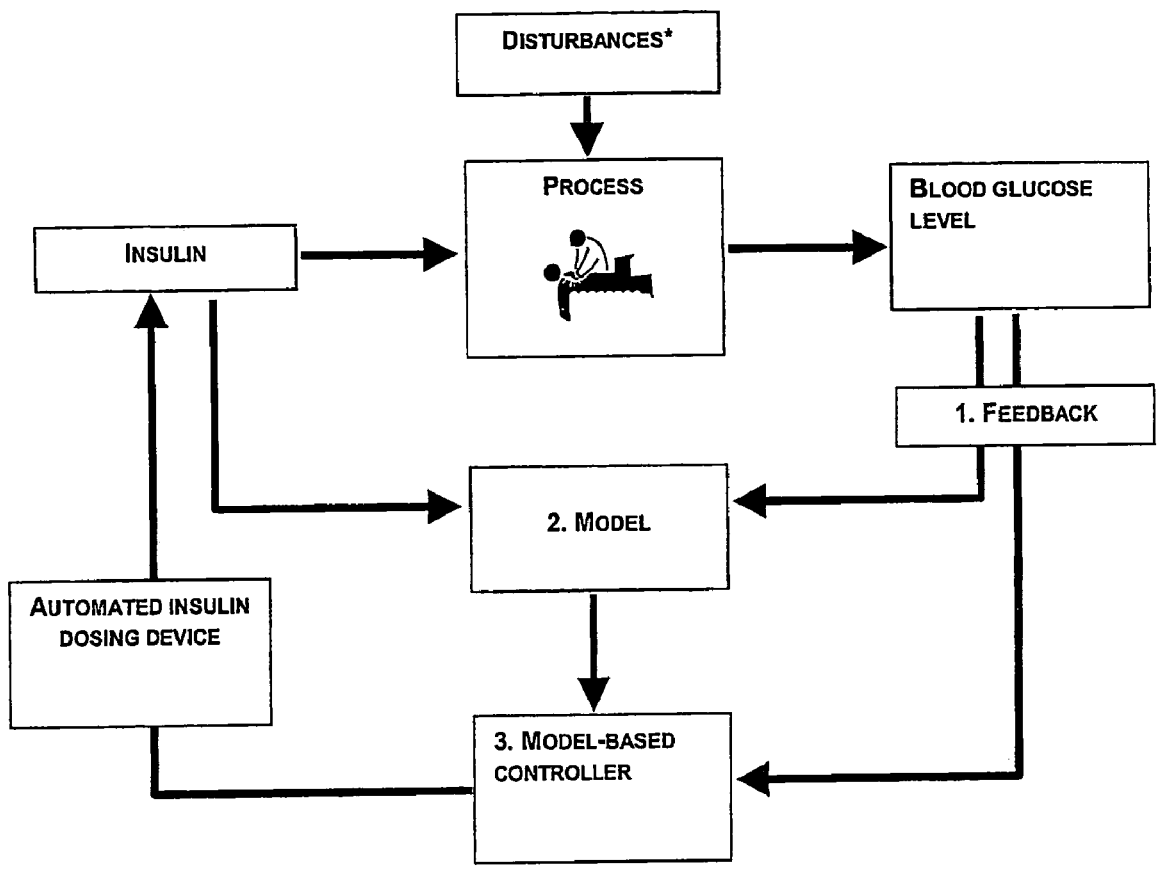

One way to control processes, such as dosing of insulin to intensive care patients, in a more optimal way is by applying model based control theory. Such control strategies require (1) continuous feedback of the process output to control and (2) the availability of a process model that predicts the dynamic response of the process output to the control input. For implementation in practice, such model should be compact and accurate. An overview of this approach applied to an efficient automated control of insulin to intensive care patients is shown in FIG. 7.

Figure 8:
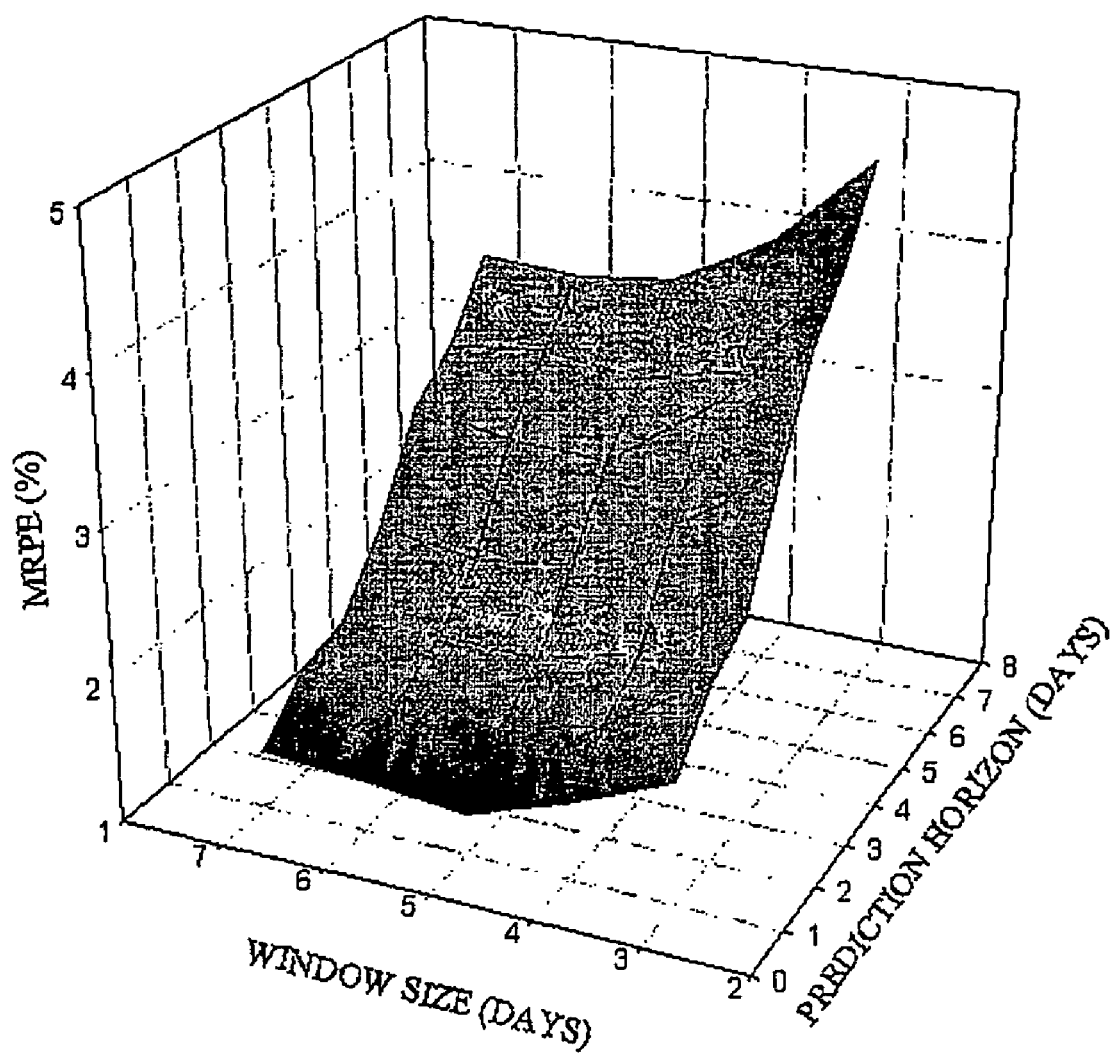

The (r)evolution in modern hardware techniques (price, computational power, reliability, compact dimensions) and software makes it possible today to use advanced mathematical techniques for modeling complex processes on-line. These modeling techniques estimate the model parameters of a mathematical model structure based on dynamic measurements of the process inputs and outputs. The estimation of the model parameters can be performed on-line during the process resulting in a dynamic model with time-variant model parameters that can cope with the dynamic, time-variant behavior of most bioprocesses. An example of the performance (in terms of mean relative prediction error MRPE) of such compact on-line model as a function of prediction horizon and time window (number of measurements used to estimate the model parameters at each time instant) is shown in FIG. 8.

In order to model the static and dynamic responses discrete transfer function models can be used, which have the following general model structure (in the single-input, single-output case:

$$y(k) = \frac{B(z^{-1})}{A(z^{-1})} u(k) + \xi(k) \quad (1)$$

with y(k)=output at time k, u(k)=input at time k,

ξ(k)=additive noise, assumed to be a zero mean, serially uncorrelated sequence of random variables with variance $\sigma^2$ accounting for measurement noise, modeling errors and effects of unmeasured inputs to the process, $A(z^{-1})=1+a_1 \cdot z^{-1}+a_2 \cdot z^{-2}+ \ldots +a_{na} \cdot z^{-na}$,
$B(z^{-1})=b_0+b_1 \cdot z^{-1}+b_2 \cdot z^{-2}+ \ldots +b_{nb} \cdot z^{-nb}$, aj, bj=model parameters to be estimated, $z^{-1}$=backward shift operator, $z^{-1} \cdot y(t) = y(t-1)$, na, nb=orders of the respective polynomials, The parameters of a transfer function (TF) model may be estimated using various methods of identification and estimation. Although Least Squares (LS) is one of the most commonly used model estimation algorithms, the estimated model parameters become asymptotically biased away from their true values in the presence of measurement or disturbance noise (Young, 1984). To avoid this bias, an instrumental variable approach can be applied. This technique makes use of prefiltered input and output variables (i.e. instrumental variables) to estimate the model parameters. Under normal conditions, the algorithm converges after three iterations resulting in parameter estimates which are asymptotically unbiased, consistent and efficient in statistical terms. The technique presented for single-input single output systems with time-invariant parameters, can also be used for multiple-input multiple-output systems and systems with time-variant parameters.

In order to obtain the control law, model predictive control (MPC) makes use of an objective function J. The general aim is that the future process output (y) on the considered horizon should follow a determined reference signal (r) and, at the same time, the control effort (Δu) necessary for doing so should be penalized. The general expression for such objective function is:

$$J(N_1, N_2, N_u) = \sum_{F=N_1}^{N_2} \delta(F)[\hat{y}(t+F \mid t) - r(t+F)]^2 + \sum_{F=1}^{N_u} \lambda(F)[\Delta u(t+F-1)]^2$$

where $N_1$ is the minimum cost horizon; $N_2$ is the maximum cost horizon; $N_u$ is the control horizon, $\hat{y}(t+F|t)$ is the predicted value of the process output y (i.e. blood glucose level) on time instant t, F time steps ahead; r(t+F) is the value of the reference trajectory (i.e. desired blood glucose level) on time instant t+F; Δu(t+F−1) is the change of the control input (i.e. insulin dose) on time instant t+F−1; δ(j), λ(j) are weighing coefficients.

Glucose Sensors

Different types of sensors (e.g., optical sensors) for frequent, fast, real time, continuous blood-glucose measurement and/or non invasive measuring glucose levels are available.

Optical measurement of glucose can, for instance, be performed by focusing a beam of light onto the body. Optical sensors can determine the glucose concentration by analyzing optical signal changes in wavelength, polarization or intensity of light. Various methods are available for accurate of the sensor measurements. One method (e.g., multivariate spectral analysis) utilizes calibration models developed by initially measuring known glucose concentrations to correct subsequent sensor measurements. The calibration models become inaccurate over time due to dynamic changes in physiological processes. Another method (e.g., adaptive noise canceling) utilizes signal processing to cancel portions of the sensor measurements unrelated to glucose concentration. For example, two substantially simultaneous sensor measurements at different wavelengths can be used to make up a composite signal which can be processed to cancel its unknown and erratic portions.

Several optical methods can be used for the continuous monitoring of glucose, but the two that show the most promise are. Fully implantable devices, measure glucose in whole blood and involve implanting a light source and detector and sending the result out of the body via a radio-frequency signal. Optochemical devices, which measure glucose via the skin's interstitial fluid and involve implanting a chemical sensor just under the skin and stimulating it with external light.

One approach of optical glucose sensing is based on the fact that glucose solutions have a magnetic optical rotatory effect such that when a magnetic field is set up in a glucose solution there is a rotation of the polarization vector of the incident light that is proportional to the path length, magnetic field strength, and the concentration of glucose in the solution.

For example, U.S. Pat. No. 5,036,861 (issued to Sembrowich et al. on Aug. 6, 1991) describes a wrist-mountable device having an electrode which measures glucose present in sweat at the skin surface.

U.S. Pat. No. 5,222,496 (issued to Clarke et al. on Jun. 29, 1993) describes an infrared glucose sensor mountable, for instance, on a wrist or finger.

U.S. Pat. No. 5,433,197 (issued to Stark on Jul. 18, 1995) describes determination of blood glucose through illuminating a patient's eye with near-infrared radiation.

U.S. Pat. Nos. 5,115,133, 5,146,091 and 5,197,951 (issued to Knudson on May 19, 1992, Sep. 8, 1992 and Jan. 19, 1993, respectively) describe measuring blood glucose within blood vessels of a tympanic membrane in a human ear through light absorption measurements.

U.S. Pat. No. 6,517,482, Nov. 1, 2000, Elden H. R. et al teaches a method and apparatus for non-invasive determination of glucose in body fluids European Patent Publication No. 0 351 891 B 1, to Hill et al., teaches a method of making an electrochemical sensor by printing. The sensor is used to detect, measure or monitor a given dissolved substrate in a mixture of dissolved substrates, most specifically glucose in body fluid.

U.S. Pat. No. 5,391,250, to Cheney et al., teaches a method of fabricating thin film electrochemical sensors for use in measuring subcutaneous or transdermal glucose. Fabrication of the sensors comprises placing a thin film base layer of insulating material onto a rigid substrate. Conductor elements for the sensors are formed on the base layer using contact mask photolithography and a thin film cover layer.

U.S. Pat. No. 5,437,999, to Diebold et al., teaches a method of fabricating thin film electrochemical devices which are suitable for biological applications using photolithography to define the electrode areas.

The disclosures of each of the above patent specifications are incorporated herein by reference in their entirety.

Different systems of implantable optical sensors are for instance available at MiniMed, BioTex, Animas, SpectRx, Dermal Therapy Inc. and Sensors for Medicine and Science Inc. Animas, for instance, developed a long-term implantable (e.g. across a vein with readings transmitted via radio waves (RF telemetry) to a small Display Unit), optical sensor suitable for continuous and accurate monitoring of blood glucose levels. This Animas sensor is based on Spectroscopy and measures the near-infrared absorption of blood and MicroSense International has developed a handheld probe that measures glucose levels without drawing blood.

Actuator

The actuator (automatic dosing device) can be an insulin pumps.

By coupling the instrument according to the invention with a pump or other device which can deliver insulin, an insulin releasing factor or other therapeutic agent to the patient, using a transmitter, or other suitable communication device, such that the pump or device is responsive to the signal input, normoglycemia monitoring may be achievable.

For example, the transmitter may remotely transmit the signal to a pump, such as a servo pump, having a receiver responsive to the transmitted signal. The pump is preferably responsive to information derived from controler.

The pump may then provide insulin or other appropriate medication to the patient. Alternately, or in addition, the information may be sent to a remote monitor.

Various infusion pump systems have been described in the current art and include U.S. Pat. No. 4,704,029, to Van Heuvelen, which teaches a blood glucose monitor which is applicable for use as an implantable unit for controlling an insulin pump.

U.S. Pat. No. 4,436,094, to Cerami, teaches a method for continuous monitoring of the glucose concentration which can be tied to an infusion device.

U.S. Pat. No. 5,665,065, to Colman et al., teaches a medication infusion device with a blood glucose data input method.

U.S. Pat. No. 5,383,865, to Michel, teaches a medication dispensing device comprising an injector attached to a cartridge with a drive mechanism.

U.S. Pat. No. 5,176,644, to Srisathapat et al., discloses a medication infusion pump with a simplified pressure reservoir.

The disclosures of the above patents are incorporated herein by reference.

TABLE 1 multivariate regression analysis of
all univariate determinants of ICU mortality

|  | OR | 95% Cl | P-value |
|---|---|---|---|
| age (per added year) | 1.036 | 1.014-1.058 | 0.001 |
| delayed ICU admission | 1.882 | 1.069-3.314 | 0.03 |
| on-admission APACHE II >9 | 5.054 | 2.524-10.120 | <0.0001 |
| reason for ICU admission |  |  |  |
| (vs. cardiac surgery OR 1) |  |  |  |
| multiple trauma or severe burns | 4.851 | 1.664-14.141 | 0.004 |
| neurological disease, cerebral trauma or brain surgery | 4.814 | 2.044-11.339 | 0.0003 |
| thoracic surgery and/or respiratory insufficiency | 2.966 | 1.242-7.084 | 0.01 |
| abdominal surgery and/or peritonitis | 2.466 | 1.017-5.979 | 0.05 |
| transplantation | 0.746 | 0.197-2.820 | 0.7 |
| vascular surgery | 1.336 | 0.433-4.123 | 0.6 |
| other | 1.904 | 0.642-5.644 | 0.2 |
| history of malignancy | 1.504 | 0.779-2.905 | 0.2 |
| on-admission hyperglycemia (|A200 mg/dl) | 1.128 | 0.601-2.116 | 0.7 |
| history of diabetes | 0.356 | 0.158-0.803 | 0.01 |
| daily insulin dose (per added unit) | 1.006 | 1.002-1.009 | 0.005 |
| mean blood glucose level (per added mg/dl) | 1015* | 1.009-1.021 | <0.0001 |

*An odds ratio of 1.015 for mean blood glucose level indicates that for every mg/dl increase in blood glucose concentration, the risk of death increases with 15 per 1000. In other words, for a blood glucose level of 200 mg/dl, the risk of death is 2.5 times higher than for a blood glucose level of 100 mg/dl.

TABLE 2 multivariate regression analysis of the impact of insulin dose
versus blood glucose level on morbidity, after correction for age,
reason for ICU admission, APACHE-II, history of malignancy
and diabetes and for on-admission hyperglycemia

|  | OR | 95% Cl | P-value |
|---|---|---|---|
| critical illness polyneuropathy |  |  |  |
| daily insulin dose (per added unit) | 0.999 | 0.995-1.003 | 0.7 |
| mean blood glucose level (per added mg/dl) | 1012* | 1.007-1.018 | <0.0001 |
| bacteremia |  |  |  |
| daily insulin dose (per added unit) | 1.000 | 0.996-1.004 | 0.9 |
| mean blood glucose level (per added mg/dl) | 1.007 | 1.001-1.014 | 0.02 |

TABLE 2-continued multivariate regression analysis of the impact of insulin dose
versus blood glucose level on morbidity, after correction for age,
reason for ICU admission, APACHE-II, history of malignancy
and diabetes and for on-admission hyperglycemia

|  | OR | 95% Cl | P-value |
|---|---|---|---|
| >3 days CRP >150 mg/l | | | |
| daily insulin dose (per added unit) | 1.004 | 1.001-1.007 | 0.02 |
| mean blood glucose level (per added mg/dl) | 1.008 | 1.003-1.012 | 0.0006 |
| acute renal failure requiring renal replacement therapy | | | |
| daily insulin dose (per added unit) | 0.994 | 0.988-1.000 | 0.03 |
| mean blood glucose level (per added mg/dl) | 1.001 | 0.994-1.007 | 0.9 |
| >2 red cell transfusions | | | |
| daily insulin dose (per added unit) | 0.998 | 0.994-1.002 | 0.3 |
| mean blood glucose level (per added mg/dl) | 1.005 | 1.000-1.011 | 0.06 |

*An odds ratio of 1.012 for mean blood glucose level indicates that for every mg/dl increase in blood glucose concentration, the risk of critical illness polyneuropathy increases with 12 per 1000. In other words, for a blood glucose level of 200 mg/dl, the risk of critical illness polyneuropathy is 2.2 times higher than for a blood glucose level of 100 mg/dl.

The invention claimed is:

1. An apparatus comprising:
a sensor to produce a signal indicative of glycemia levels in a patient, said patient characterized by a patient profile,
a programmable actuator adapted to deliver a blood glucose regulator to said patient at an administration rate and
a control system adapted to regulate said administration rate of said blood glucose regulator,
wherein a model-based predictive controller based on an adaptive dynamic patient model predicts a future response of said patient's glycemia to said administration rate of said blood glucose regulator as a function of time and compensates effects of external disturbance on said patients' glycemia by adjusting said administration rate of said blood glucose regulator to achieve a status of normoglycemia in said patient, which is a critically ill patient and
wherein said adaptive dynamic patient model comprising parameter settings corresponds to a model for which:
in an initial phase, the parameter settings are determined based on the patient profile comprising variables including on-admission parameters, which determine the class of the patient, whereby each class is associated with distinct parameters for the model; and
after the initial phase, the parameter settings are adapted by the incoming signal to more closely approximate the dynamic behaviour of the glycemia in the patient.

2. The apparatus of claim 1, wherein the controller proactively compensates a future effect of known current or future disturbances by using said adaptive dynamic patient model in order to minimise deviation from normoglycemia.

3. The apparatus of claim 1, wherein the control system furthermore comprises a continuous feedback of said patients' glycemia to control.

4. The apparatus of claim 1, wherein the controller is a feedback controller based on an adaptive dynamic patient model.

5. The apparatus of claim 1, wherein the external disturbance is one selected from the group of disturbances consisting of: change in kind of medication, dose of medication, means of administration of medication, and change in caloric intake.

6. The apparatus of claim 1, wherein said adaptive dynamic patient model is based on a low-order (N)ARX-model.

7. The apparatus of claim 1, wherein said adaptive dynamic patient model is based on a state-space model.

8. The apparatus of claim 1, wherein said profile of said critically ill patient further comprises one or more of the following variables: BMI, prior history of diabetes, reason for ICU admission.

9. The apparatus of claim 1, wherein said on-admission parameters are selected from the group consisting of: APACHE-II on admission, on-admission glycemia, caloric intake on admission, concomitant medication on admission.

10. The apparatus of claim 1, wherein prefiltered input and output variables (i.e. instrumental variables) are used to estimate the model parameters.

11. A method for the treatment of a critically ill patient under a condition of insulin resistance or under a condition of increased glucose turnover, which comprises administering to a critically ill patient, characterized by a patient profile, a blood glucose regulator using an apparatus comprising:
a sensor to produce a signal indicative of the glycemia levels in said patient;
a programmable actuator adapted to deliver said blood glucose regulator to said patient at an administration rate; and
a control system adapted to regulate the administration level rate of said blood glucose regulator,
wherein said apparatus comprises a model-based predictive controller based on an adaptive dynamic patient model which predicts a future response of said patient's glycemia to said administration rate of said blood glucose regulator as a function of time and compensates effects of external disturbance on said patient's glycemia by adjusting said administration rate of said blood glucose regulator to achieve a status of normoglycemia in said critically ill patient and
wherein said adaptive dynamic patient model comprising parameter settings corresponds to a model for which:
in an initial phase, the parameter settings are determined based on the patient profile comprising variables including on-admission parameters, which determine the class of the patient, whereby each class is associated with distinct parameters for the model; and
after the initial phase, the parameter settings are adapted by the incoming signal to more closely approximate the dynamic behaviour of the glycemia in the patient.

12. The method of claim 11, wherein the blood glucose regulator is selected from insulin, an insulin analogue, an active derivative of insulin or a monomeric human insulin analogue.

13. The method of claim 11, wherein said blood glucose regulator is selected from the group consisting of: glucagon like peptide 1 (a GLP-1), a GLP-1 analog, GLP-1 derivatives and pharmaceutically acceptable salts thereof, somatostatin, gastric inhibitor polypeptide, glucose-dependent insulinotropic peptide, bombesin, calcitonin gene-related peptide, gastrin-releasing peptide, cholinergic agonists, isoproterenol, and bethanechol.

14. The method of claim 11, wherein hyperglycemia is reduced to stable normoglycemia in a critically ill patient without causing hypoglycemia in an initial phase of less than 24 hours and normoglycemia is maintained under changing conditions of said critically ill patient (e.g., decreasing insulin resistance, other route of feeding, change in medication) or complications of said critically ill patient (e.g., concomitant infection).

15. The method of claim 11, wherein said apparatus is configured to maintain blood glucose between 60 mg/dl and 130 mg/dl in said critically ill patient.

16. The method of claim 11, wherein said apparatus is configured to maintain blood glucose between 80 and 110 mg/dl in said critically ill patient.

17. A method for the treatment of a critically ill patient, to prevent or decrease the incidence of blood stream infection, to reduce morbidity and mortality in the critical care, to prevent or decrease the incidence of prolonged inflammation, to prevent or decrease the incidence of acute renal failure, to prevent or decrease the incidence of polyneuropathy, to prevent or decrease the incidence of immune-mediated destruction of the beta cells, to prevent or decrease the incidence of systemic inflammatory response syndrome (SIRS) to prevent or decrease the incidence of sepsis, to prevent or decrease the incidence of endoneural edema, to prevent or decrease the incidence of phrenic nerves or to decrease dialysis or hemofiltration, which comprises administering a blood glucose regulator to a critically ill patient, characterized by a patient profile, using an apparatus comprising:

a sensor to produce a signal indicative of the glycemia levels in said patient;

a programmable actuator adapted to deliver a blood glucose regulator to said patient at an administration rate; and a control system adapted to regulate the administration rate of said blood glucose regulator;

wherein said apparatus comprises a model-based predictive controller based on an adaptive dynamic patient model which predicts a future response of the patient's glycemia to said administration rate of said blood glucose regulator as a function of time and compensates effects of external disturbance on said patient's glycemia by adjusting said administration rate of the blood glucose regulator to achieve a status of normoglycemia in said critically ill patient and wherein said adaptive dynamic patient model comprising parameter settings corresponds to a model for which:

in an initial phase, the parameter settings are determined based on the patient profile comprising parameters including on-admission parameters, which determine the class of the patient, whereby each class is associated with distinct parameters for the model; and after the initial phase, the parameter settings are adapted by the incoming signal to more closely approximate the dynamic behaviour of the glycemia in the patient.

* * * * *